(12) United States Patent
Matsushita et al.

(10) Patent No.: US 7,906,344 B2
(45) Date of Patent: *Mar. 15, 2011

(54) LOCALIZED PLASMON RESONANCE SENSOR AND EXAMINING DEVICE

(75) Inventors: Tomohiko Matsushita, Hirakata (JP); Shigeru Aoyama, Kyoto (JP); Takeo Nishikawa, Kyotanabe (JP); Shingo Nagaoka, Nara (JP); Tetsuichi Wazawa, Sendai (JP)

(73) Assignee: OMRON Corporation, Kyoto (JP)

( * ) Notice: Subject to any disclaimer, the term of this patent is extended or adjusted under 35 U.S.C. 154(b) by 864 days.

This patent is subject to a terminal disclaimer.

(21) Appl. No.: 10/594,698

(22) PCT Filed: Mar. 30, 2005

(86) PCT No.: PCT/JP2005/006116
§ 371 (c)(1), (2), (4) Date: Jul. 18, 2007

(87) PCT Pub. No.: WO2005/095927
PCT Pub. Date: Oct. 13, 2005

(65) Prior Publication Data
US 2007/0273884 A1     Nov. 29, 2007

(30) Foreign Application Priority Data
Mar. 31, 2004   (JP) ................... 2004-102017

(51) Int. Cl.
*G01N 33/553* (2006.01)
(52) U.S. Cl. .......... 436/525; 385/12; 385/129; 385/130; 422/82.11; 435/287.2; 435/288.7; 435/808; 436/164; 436/524; 436/805

(58) Field of Classification Search ........................ None
See application file for complete search history.

(56) References Cited

U.S. PATENT DOCUMENTS
4,877,747 A * 10/1989 Stewart ..................... 436/525
(Continued)

FOREIGN PATENT DOCUMENTS
JP        6-27023         2/1994
(Continued)

OTHER PUBLICATIONS
Patent Abstracts of Japan, Publication No. 2001-021565, Publication Date: Jan. 26, 2001, 1 page.
(Continued)

*Primary Examiner* — Christopher L Chin
(74) *Attorney, Agent, or Firm* — Osha • Liang LLP

(57) ABSTRACT

The metal fine particles 33 are sparsely fixed on the surface of the transparent substrate 32, and the acceptor 35 for attaching the specific ligand is immobilized on the transparent substrate 32 or the metal fine particles 33. The prism 36 is closely attached to the lower surface of the transparent substrate 32, and the excitation light enters the transparent substrate 32 through the prism 36. The incident light is totally reflected at the surface of the transparent substrate 32, and the evanescent light generated at the surface and the metal fine particles 33 locally plasmon resonate. As the evanescent light and the metal fine particles locally plasmon resonate, a strong electric field is enclosed in the vicinity of the metal fine particles. When the surface arranged with the metal fine particles 33 and the acceptor 35 is contacted to the analysis sample solution containing ligand modified with light emitting molecules, only the light emitting molecule modifying a specific ligand attached to the acceptor emits light.

15 Claims, 21 Drawing Sheets

U.S. PATENT DOCUMENTS 5,527,712 A * 6/1996 Sheehy .................... 436/525
6,331,276 B1 * 12/2001 Takei et al. ............. 422/82.09

FOREIGN PATENT DOCUMENTS

| | | |
|---|---|---|
| JP | 11-218491 | 8/1999 |
| JP | 2000-131237 | 5/2000 |
| JP | 2000-356587 | 12/2000 |
| JP | 2001-021565 A | 1/2001 |
| JP | 2002-62255 | 2/2002 |
| JP | 2002-116149 A | 4/2002 |
| JP | 2002-277397 | 9/2002 |
| JP | 2002-365210 | 12/2002 |
| JP | 2003-121349 | 4/2003 |
| JP | 2003-156504 | 5/2003 |
| JP | 2003-270132 | 9/2003 |

OTHER PUBLICATIONS

Patent Abstracts of Japan, Publication No. 2001-116149, Publication Date: Apr. 19, 2002, 1 page.
Notification of Reasons for Rejection for Japanese Application No. 2006-511746 mailed on Sep. 17, 2009 and English translation thereof, 7 pages.
International Search Report for PCT/JP2005/006116 dated Jun. 21, 2005 (2 pages).
Patent Abstracts of Japan 2000-131237 dated May 12, 2000 (2 pages).
Patent Abstracts of Japan 2000-356587 dated Dec. 26, 2000 (2 pages).
Patent Abstracts of Japan 2006-027023 dated Feb. 4, 2006 (2 pages).

* cited by examiner (a)

(b)

(c)

Excitation light

Interface

Interface
(Metal thin film)

Interface
(Metal fine
particles)

(a)

(b)

(a)

(b)

(a)

(b)

LOCALIZED PLASMON RESONANCE SENSOR AND EXAMINING DEVICE

TECHNICAL FIELD

The present invention relates to localized plasmon resonance sensors, in particular, to a localized plasmon resonance sensor suited for detecting a specific ligand, antigen and the like, and an examining device.

BACKGROUND ART

Recently, surface plasmon sensor, localized plasmon sensor, or total reflection fluorescent lighting sensor is used as a sensor for detecting the presence or the extent of biomolecular interaction.

FIG. 1 is a schematic diagram showing a conventional total reflection fluorescent lighting sensor 11. In the total reflection fluorescent lighting sensor 11, a metal thin film 13 such as Au thin film and the like is formed on the upper surface of a transparent substrate 12 made of glass etc., and a great number of acceptors 14 are immobilized on the metal thin film 13. A prism 16 is closely attached to the lower surface of the transparent substrate 12.

The total reflection fluorescent illumination sensor 11 is arranged so that the acceptors 14 directly contact a flow path 17 through which the analysis sample solution flows. The ligand 15 in the analysis sample solution is modified with fluorescent molecules in advance. The excitation light exits from a light source 18 towards the prism 16 so that an incident angle at the interface between the transparent substrate 12 and the metal thin film 13 becomes an angle greater than the total reflection angle at the relevant interface. The excitation light that has passed the prism 16 and the transparent substrate 12 is totally reflected at the interface of the metal thin film 13 and the transparent substrate 12. The evanescent light is then generated at the back surface of the metal thin film 13, and the electric field of the evanescent light transmits through the metal thin film 13 and the acceptors 14 and spreads. Furthermore, a greater electric field is generated by the surface plasmon in the metal thin film 13 excited by the evanescent light. The electric field generated by the evanescent light and the surface plasmon excites the fluorescent molecules of the ligand 15 bonded to the acceptor 14 and light is emitted. The presence of a specific ligand 15 bonded to the acceptor 14, or the amount of the ligand 15 bonded to the acceptor 14 can be measured by measuring the emission intensity by means of a light detector 19 arranged facing the acceptor 14.

However, since the electric field generated by the evanescent light and the like diffuses up to the distance of 200 to 300 nm from the surface of the transparent substrate 12, as shown in FIG. 1, not only the ligand 15 bonded to the acceptor 14, but even the fluorescent molecules of the ligand 15 not bonded to the acceptor 14 are excited, which becomes a noise in the measured data. Particularly, the noise becomes larger the higher the concentration of the ligand 15 in the analysis sample solution. The noise becomes the cause of significant lowering in the measurement accuracy of the total reflection fluorescent illumination sensor since the size of the biomolecules is a several tens of nm, and thus the detection accuracy of about one molecule of analyte is difficult to obtain.

FIG. 2 is a schematic diagram showing a conventional localized plasmon resonance sensor 21 (patent article 3). In the localized plasmon resonance sensor 21, a great number of metal fine particles 23 of Au and the like having a diameter of 10 to 20 nm are fixed on one surface of the transparent substrate 22 made of glass etc. to configure a sensor unit 24. The light beam is irradiated perpendicular to the sensor unit 24 from the light source 25 on the side opposite the surface fixed with the metal fine particles 23, and the absorption spectrum of the light that has transmitted through the metal fine particles 23 is measured with a spectrophotometer 26 to obtain the absorbance. A strong absorption peak appears for the light near the wavelength of 520 nm in such localized plasmon resonance sensor 21.

In the localized plasmon resonance sensor 21, the change in index of refraction at the vicinity of the metal fine particles can be detected from the change in absorbance. As shown in FIG. 3, when the acceptor 27 is immobilized to the surface of the metal fine particles 23 fixed to the transparent substrate 22 of the sensor unit 24, the presence or the amount of the specific ligand 28 can be detected since the index of refraction at the periphery of the metal fine particles 23 changes and the absorbance of the light that has transmitted through the metal fine particles 23 changes if a specific ligand 28 is attached to the acceptor 27.

In such localized plasmon resonance sensor, the prism as in the total reflection fluorescent illumination sensor is not necessary and miniaturization is possible since the absorptivity of the transmitted light that has transmitted through the metal fine particles is being measured. Furthermore, when the metal fine particles are used, only the change in the vicinity of the metal fine particles can be detected since the electric field localizes as opposed to the metal thin film (total reflection fluorescent illumination sensor), whereby measurement of the analyte in a small region becomes possible and the influence of the analyte at a location distant from the metal fine particles can be reduced.

However, the change in index of refraction is very small according to this method, and thus the change in absorbance is also very small. Therefore, the detection accuracy of about one molecule is difficult to obtain even with such localized plasmon resonance sensor.

[Patent article 1] Japanese Laid-Open Patent Publication No. 2000-131237

[Patent article 2] Japanese Patent No. 3452837

[Patent article 3] Japanese Laid-Open Patent Publication No. 6-27023

DISCLOSURE OF THE INVENTION

The present invention, in view of the above problems, aims to provide a localized plasmon resonance sensor of a novel configuration that enhances the detection accuracy compared to the prior art, and an examining device.

A localized plasmon resonance sensor according to the present invention includes a sensor unit having a metal layer with convex parts or concave parts formed on a surface of a transparent substrate and molecule recognition functional substance for attaching a specific analyte immobilized on the substrate or the metal layer; where the surface arranged with the metal layer and the molecule recognition functional substances of the sensor unit is contacted to an analysis sample solution containing analyte modified with a light emitting molecule, and an excitation light is irradiated onto the other surface of the sensor unit. The analyte herein refers to ligand or antigen, but is not limited to biomolecules. The molecule recognition functional substance functions to selectively bond the specific analyte, and includes proteins such as acceptors, antibodies, enzymes and the like. The relevant sensor can be used as a biosensor if biopolymer is used as the molecule recognition functional substance, but is not limited to biopolymers in the localized plasmon resonance sensor. The light emitting molecule only needs to be able to generate luminescent light of fluorescent, phosphorescence and the like when irradiated with light or electromagnetic field, and may be fluorescein, thiofuran, eosin, rhodamine B etc.

The convex part is such in which the distance (size of intermediate space) between the convex parts is greater than one times the outside dimension of the convex part when seen from vertically above, and in particular, the average value of the distance between the convex parts is desirably greater than or equal to two times and less than or equal to four times the outside dimension of the convex part. Similarly, the concave part is such in which the distance (size of intermediate space) between the concave parts is greater than one times the outside dimension of the concave part when seen from vertically above, and in particular, the average value of the distance between the concave parts is desirably greater than or equal to two times and less than or equal to four times the outside dimension of the concave part. The localized plasmon resonance is efficiently generated by having the distance between the convex parts or the concave parts to greater than or equal to two times and less than or equal to four times the outside dimension.

Since the analyte is modified with the light emitting molecule in the localized plasmon resonance sensor of the present invention, when the specific analyte is contained in the analysis sample solution and such specific analyte is attached to the molecule recognition functional substance, the light emitting molecule modifying the specific analyte is captured in the vicinity of the metal layer. When the excitation light is irradiated onto the metal layer at this state, the localized plasmon is excited at the convex parts or the concave parts of the metal layer, and a strong electric field is generated at the periphery thereof. Thus, the light emitting molecule emits the luminescent light if the light emitting molecule is captured in the vicinity. Therefore, the presence and the amount of the specific analyte attached to the molecule recognition functional substance can be measured by observing the luminescent light.

Furthermore, in the localized plasmon resonance sensor, a strong signal is obtained and the measurement accuracy of the specific analyte is enhanced since the light emission of the captured light emitting molecule is observed. Furthermore, since the metal layer with the convex parts or the concave parts is formed on the transparent substrate, the electric field is localized in a small region around the convex part or the concave part of the metal layer when the excitation light is irradiated, and the electric field does not spread to a wide range (diffusing distance) of 200 to 300 nm as when the metal thin film of even thickness is arranged. Therefore, the light emitting molecule that emits light reduces at the analyte not captured at the molecule recognition functional substance, and the noise of the signal reduces. As a result, in the localized plasmon resonance sensor of the present invention, high S/N ratio is obtained and high measurement accuracy is achieved by the combination of the light emitting molecule for modifying the analyte and the metal layer with the convex parts or the concave parts. In particular, detection of one molecule of analyte captured at the molecule recognition functional substance becomes possible.

In one embodiment of the present invention, the excitation light is irradiated onto the sensor unit at an incident angle totally reflected at the surface of the substrate. When the excitation light is totally reflected at the surface of the substrate, the totally reflected excitation light diffuses from the surface of the substrate to the metal layer side and becomes the evanescent light, whereby the evanescent light and the convex parts or the concave parts of the metal layer bond thereby enhancing the bonding efficiency of the excitation light and the convex part or the concave part. As the bonding efficiency of the excitation light and the convex parts or the concave parts enhances, the intensity of the electric field generated around the convex part or the concave part increases.

Furthermore, in the present embodiment, the prism is desirably arranged closely attached to the back surface of the substrate. A triangular prism, a semicircular or semispherical prism (glass block) may be used for the prism depending on the measurement mode. The reflection of the excitation light is reduced and the excitation light is efficiently guided to the substrate by arranging the prism closely attached to the back surface of the substrate.

In another embodiment of the present invention, a light detector is arranged by way of a lens on the side facing the surface arranged with the metal layer and the molecule recognition functional substances of the sensor unit. The light emission of a narrow region can be observed and the resolution of about one molecule of analyte is obtained by observing the evanescent light of the light emitting molecule by means of the light detector through the lens (e.g., objective lens, microscopic optical system etc.).

The wavelength of the excitation light is desirably different from the emission wavelength of the light emitting molecule. By differing the wavelength of the excitation light and the emission wavelength of the light emitting molecule, the excitation light and the evanescent light of the light emitting molecule are easily separated, thereby enhancing the measurement accuracy. In this case, a cut filter for shielding the excitation light and transmitting only the light of the emission wavelength of the light emitting molecule may be arranged in front of the light detector. The excitation light is prevented from entering the light detector by arranging the cut filter, and thus the noise of the measurement signal is further reduced.

The metal layer with the convex parts used in the present invention is desirably made of metal particles fixed spaced apart from each other on the surface of the substrate, but may have the metal fine particles fixed spaced apart from each other on the metal thin film formed on the surface of the substrate. Alternatively, the metal thin film may be formed on the surface of the substrate from above the metal fine particles fixed spaced apart from each other on the surface of the substrate. Furthermore, the metal layer with the concave parts includes the concave parts formed spaced apart from each other in the metal thin film formed on the surface of the substrate. The convex parts or the concave parts may be formed by embossing the metal thin film formed on the surface of the substrate with a stamper.

The material of the metal layer is desirably Au or Ag. Other metal materials may also be used, but if Au or Ag is used, localized plasmon resonance is efficiently generated in the visible light range, and the metal layer and the molecule recognition functional substances are less likely to react and thus satisfactory stability is achieved.

The height (depth) and the width of the convex part or the concave part are both less than or equal to 150 nm to efficiently generate the localized plasmon resonance. The shape of the convex part is a sphere, an elliptical sphere, or one part of the sphere or the elliptical sphere to efficiently generate the localized plasmon resonance.

In another further embodiment of the present invention, hydrophilic process, hydrophobic process, or charging process is performed on one region of the substrate or the metal layer, and the molecule recognition functional substances are immobilized at the region not performed with the process. Since the biomolecules such as protein have a property of being hydrophilic, hydrophobic, or charged, the biomolecules can be arrayed at the desired region as the molecule recognition functional substance by performing hydrophilic process, hydrophobic process, or charging process on the predetermined region of the substrate, thereby facilitating the alignment of the molecule recognition functional substances.

The mol concentration of the light emitting molecule in the analysis sample solution can be measured at greater than or equal to 100 nM (=$10^{-7}$ mol/liter), and thus measurement of the analyte can be performed at the biological analyte concentration.

A flow path for passing the analysis sample solution is arranged in the localized plasmon resonance sensor, and the molecule recognition functional substances are arranged facing the inside of the flow path, so that the analysis sample solution is easily guided to the region immobilized with the molecule recognition functional substances.

In another further embodiment of the present invention, the sensor unit includes a plurality of regions to be introduced with the analysis sample solution, and each region is immobilized with the molecule recognition functional substance different from each other. According to such embodiment, a plurality of different examinations can be simultaneously performed.

An examining device of the present invention includes the localized plasmon resonance sensor according to the present invention and a means for analyzing the analysis sample solution based on the output data of the sensor. According to the examining device, the presence and the amount of the specific analyte attached to the molecule recognition functional substance can be measured at high S/N ratio by observing the luminescent light emitted by the light emitting molecule.

The measurement method of the present invention is measurement method using a localized plasmon resonance sensor including a sensor unit having a metal layer with convex parts or concave parts formed on a surface of a transparent substrate and molecule recognition functional substance for attaching a specific analyte immobilized on the substrate or the metal layer; the method including the steps of forming an analysis sample solution by mixing a solution to be measured and a light emitting molecule; contacting the sample solution to the surface arranged with the metal layer and the molecule recognition functional substances of the sensor unit; irradiating an excitation light to a surface not arranged with the metal layer and the molecule recognition functional substances of the sensor unit; detecting emission intensity of the light emitting molecule light emitted by an electric field generated by the excitation light; and calculating the presence and the concentration of the analyte from the emission intensity. The object to be measured is mainly biomolecules, and, includes at least one of gene, protein, sugar chain or cell among the biomolecules. For example, the body fluid of human or animal may be the solution to be measured. However, the object to be measured is not necessarily limited to biomolecules. The molecule recognition functional substance functions to selectively bond the specific analyte, and includes proteins such as acceptors, antibodies, enzymes and the like. The relevant sensor can be used as a biosensor if biopolymer is used as the molecule recognition functional substance, but is not limited to biopolymers in the localized plasmon resonance sensor. The light emitting molecule only needs to be able to generate luminescent light of fluorescent, phosphorescence and the like when irradiated with light or electromagnetic field, and may be fluorescein, thiofuran, eosin, rhodamine B etc.

According to the measurement method, the presence and the amount of the specific analyte attached to the molecule recognition functional substance can be measured at high S/N ratio by observing the luminescent light emitted by the light emitting molecule, similar to the localized plasmon resonance sensor.

The components described above in the present invention may be arbitrarily combined wherever possible.

BRIEF DESCRIPTION OF THE DRAWINGS

The invention, together with objects and advantages thereof, may best be understood by reference to the following description of the presently preferred embodiment together with the accompanying drawings in which.

BEST MODE FOR CARRYING OUT THE INVENTION

The embodiments of the present invention will now be described in detail according to the drawings. It should be recognized that the present invention is not limited to the following embodiments.

Figure 1:
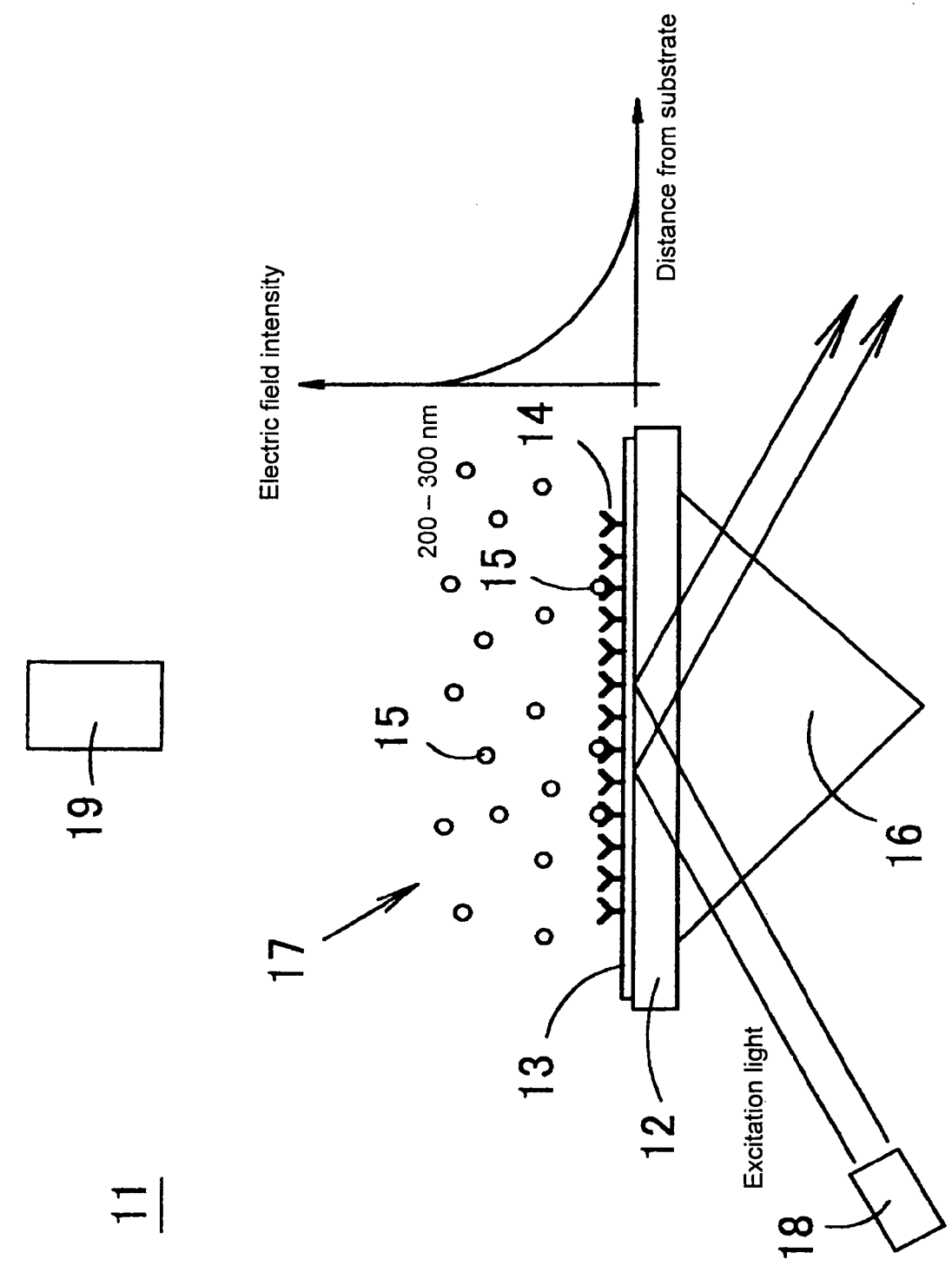
FIG. 1 is a schematic diagram showing a conventional total reflection fluorescent illumination sensor.
Figure 2:
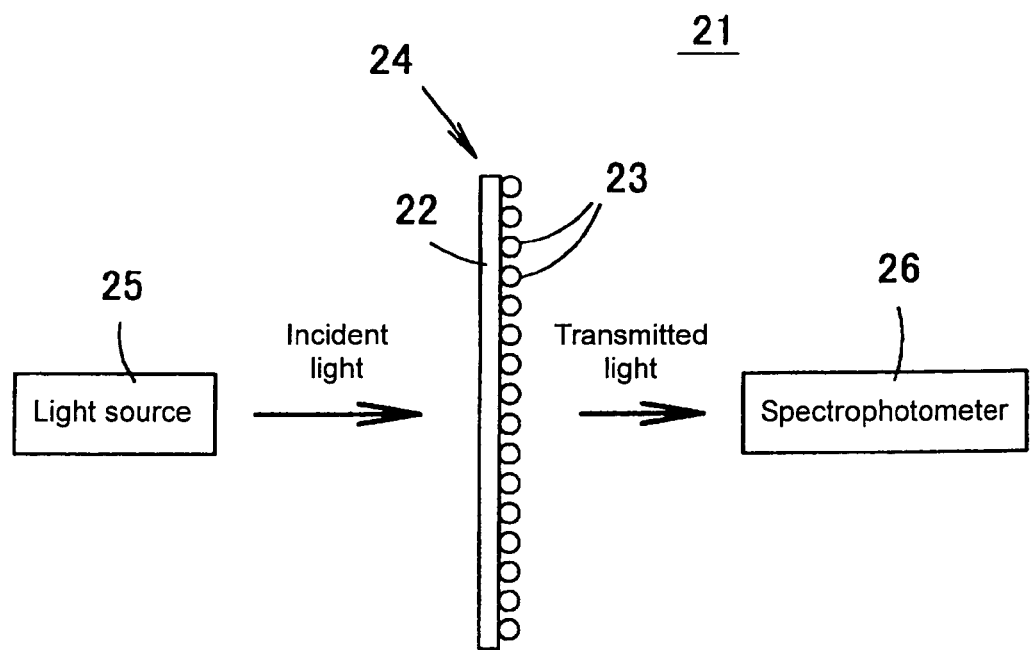
FIG. 2 is a schematic diagram showing a conventional localized plasmon resonance sensor.
Figure 3:
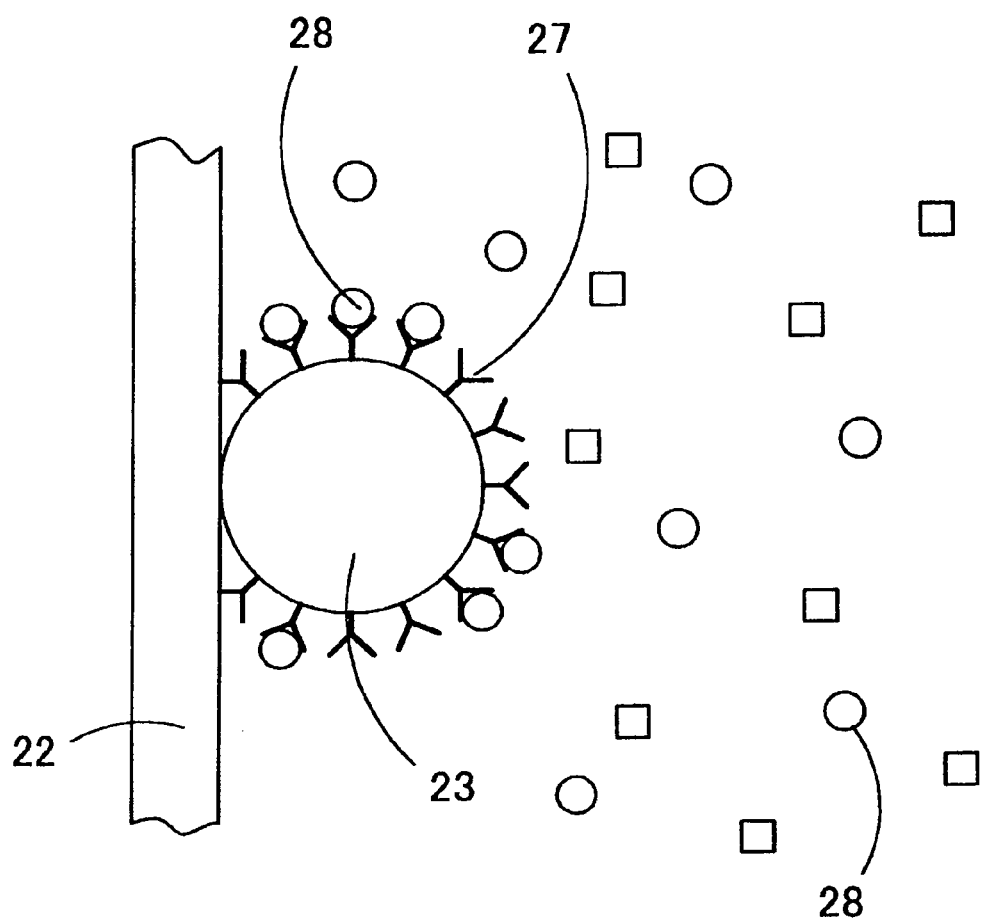
FIG. 3 is a view showing a state in which a ligand is attached to an acceptor immobilized to the surface of the metal fine particles of a transparent substrate in the localized plasmon sensor of FIG. 2.
Figure 4:
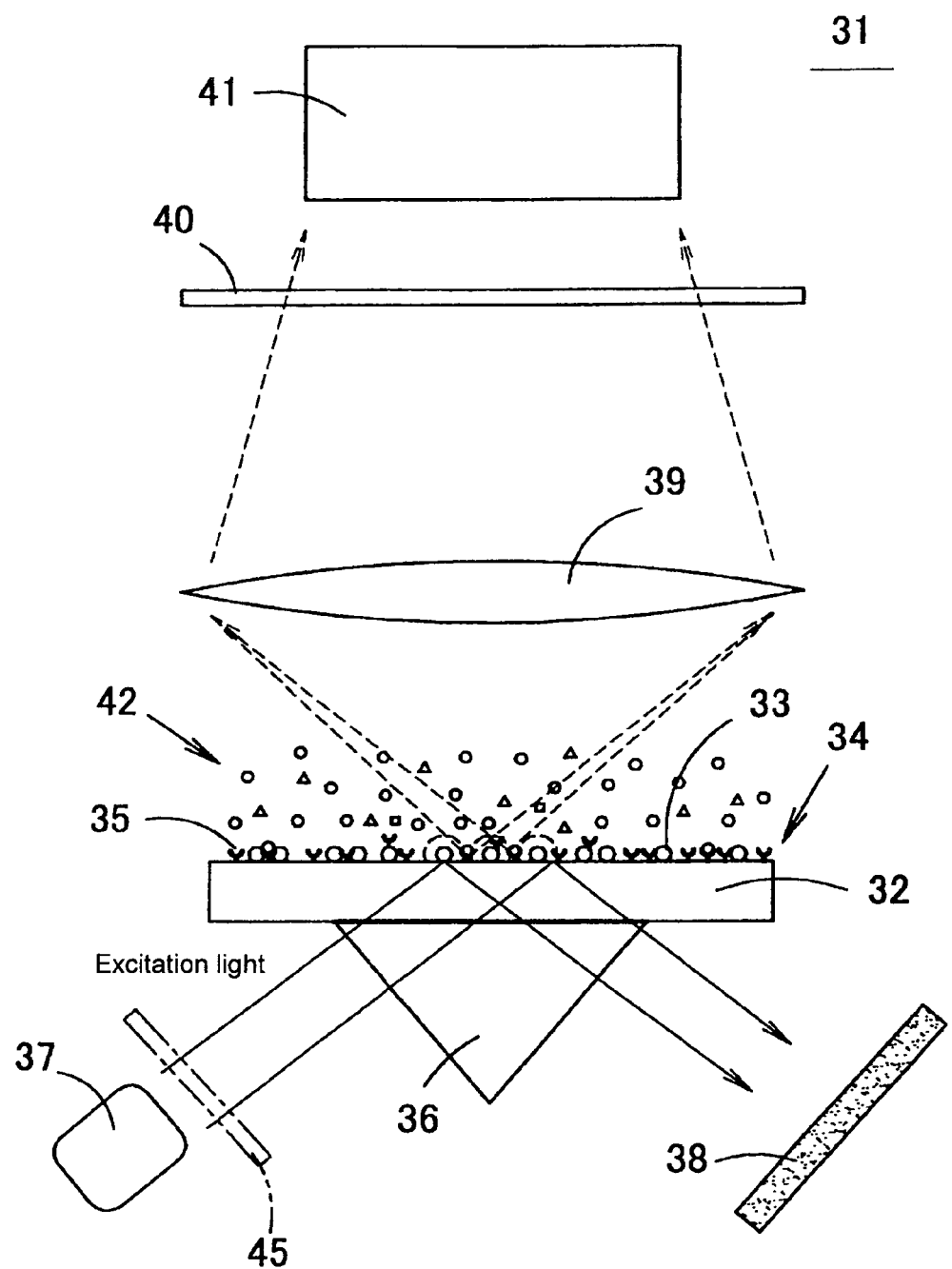
FIG. 4 is a schematic configuration view of a localized plasmon resonance sensor according to one embodiment of the present invention.
Figure 5:
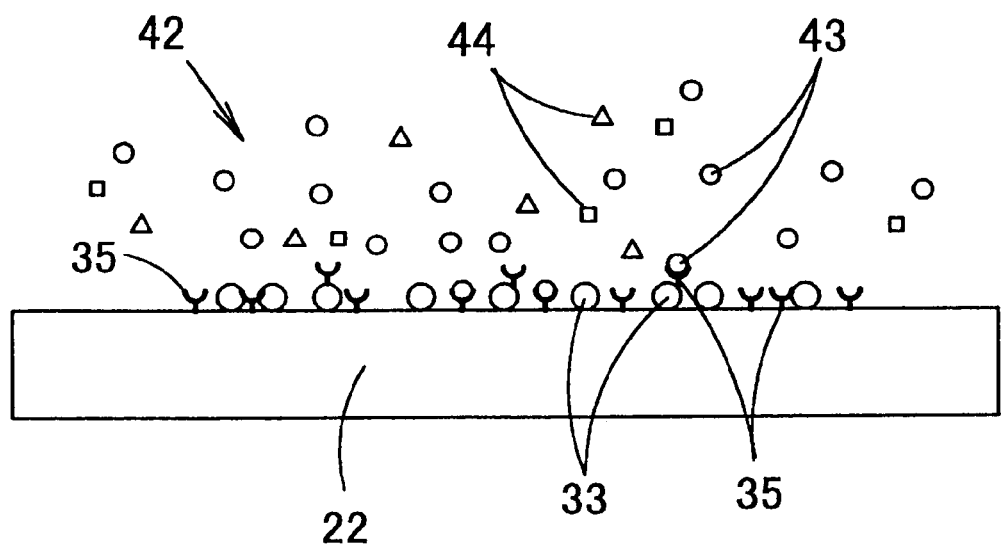
FIG. 5 is a schematic diagram enlarging one part of FIG. 4.

FIG. 4 is a schematic configuration view of a localized plasmon resonance sensor 31 according to one embodiment of the present invention, and FIG. 5 is a schematic view enlarging one part thereof. The localized plasmon resonance sensor 31 mainly includes a sensor unit 34, a light source 37 and a light detector 41. In the sensor unit 34, a great number of metal fine particles 33 are fixed on the surface of the transparent substrate 32 made of glass substrate and the like to form a metal layer. The metal fine particles 33 are metal particles of nano level of Au, Ag and the like having a diameter of a several tens nm (in particular diameter of 10 to 30 nm), which are fixed separated from each other without barely aggregating. The arrangement of the metal fine particles 33 do not need to be orderly, and may be randomly dispersed.

The metal fine particles 33 desirably have the distance (size of intermediate space) from each other of greater than or equal to two times and less than or equal to four times the diameter of the metal fine particles 33. For example, assuming about 370 are present per 1 μm², the density of the metal fine particles 33 becomes about 0.17 when converted to coverage. A predetermined type of acceptor 35 is also immobilized as a molecule recognition functional substance on the surface of the transparent substrate 32 and the metal fine particles 33.

The acceptor 35 may be immobilized at one region of the transparent substrate 32 or may be divisionally immobilized. Furthermore, one type of acceptor 35 may be used, or two or more types of acceptor 35 may be sorted and immobilized. When immobilizing the acceptor 35 at one part of the transparent substrate 32, pre-processes such as hydrophilic process, hydrophobic process, or charging process may be performed on the region other than the region to be immobilized with the acceptor 35. Silane coupling agent and the like may be used as the pre-process agent therefor. A method of performing the pre-process includes methods such as medical agent application by ink jet printer, coating formation by photolithography, charging process by laser irradiation, electron beam irradiation etc. Since the acceptor 35, which is a biopolymer, has a property of being charged, hydrophilic, hydrophobic and the like, the acceptor 35 will not immobilize at the region other than the region to be immobilized with the acceptor 35 if one of the pre-processes is performed according to the property of the acceptor 35.

The upper surface of a prism 26 is closely attached to the back surface of the transparent substrate 32 by way of matching oil and the like. In the figure, the upper surface of the triangular prism is closely attached to the back surface of the transparent substrate 32, but the prism (glass block) of semicircular shape or semispherical shape may be closely attached to the back surface of the transparent substrate 32 when changing the incident angle of the incident light and performing the measurement.

A light source 37 for exiting the excitation light (light of wavelength region that can excite the light emitting molecule for light emission, to be hereinafter described), and a light absorbing plate 38 of black plate and the like are arranged on the back surface side of the sensor unit 34. Semiconductor laser (LD), light emitting diode (LED), lamp etc. are used as the light source 37. The wavelength of the light exiting from the light source 37 may have a wavelength region different from the emission wavelength of the light emitting molecule. Alternatively, a filter 45 is arranged at the front of the light source 37, so that the filter 45 removes the light of the emission wavelength region of the light emitting molecule out of the light exiting from the light source 37. The light source 25 is arranged so that the exited light enters the surface of the transparent substrate 32 at an incident angle greater than the total reflection angle.

A lens 39 such as objective lens, microscopic optical system or the like, a cut filter 40 for shielding the light of the wavelength of the excitation light and transmitting the light of the emission wavelength band of the light emitting molecule, and a light detector 41 such as photodiode (PD) and CCD are arranged in this order facing the surface of the transparent substrate 32 arranged with the metal fine particles 33 and the acceptors 35.

Figure 6:
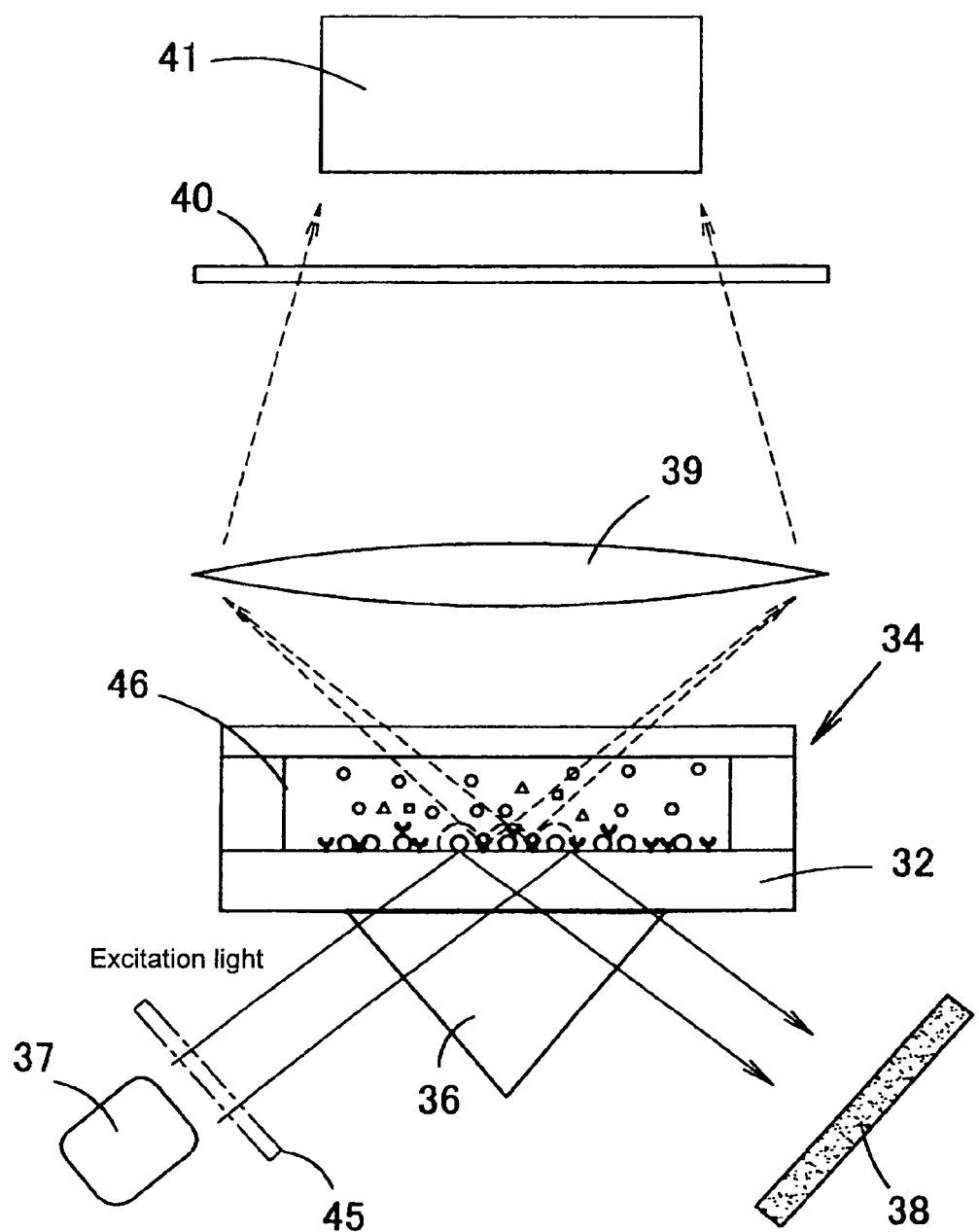
FIG. 6 is a schematic configuration view showing a variant of the localized plasmon sensor of the present invention.

The analysis sample solution 42 is introduced to the surface side of the transparent substrate 32, allowing the analysis sample solution 42 to contact the acceptor 35. In order to easily introduce the analysis sample solution 42, a flow path 46 through which the analysis sample solution 42 flows is desirably formed on the surface side of the transparent substrate 32, as shown in FIG. 6. The upper surface of the flow path 46 is covered in FIG. 6, but the upper surface of the flow path 46 may also be opened. The analysis sample solution 42 is body fluid such as blood of a human or an animal, and the ligand contained therein is modified in advance by the light emitting molecule. The light emitting molecule is such that generates the luminescent light of fluorescent, phosphorescent etc. when irradiated with light or electromagnetic field, and may be fluorescein, thiofuran, eosin, rhodamine B etc.

However, in the localized plasmon resonance sensor 31, the analysis sample solution 42 contacts the acceptor 35 when the analysis sample solution 42 containing the ligand is introduced to the surface side of the transparent substrate 32. As shown in FIG. 5, when a specific ligand 43 that bonds to the acceptor 35 is contained in the analysis sample solution 42 introduced to the surface side of the transparent substrate 32a, part of the specific ligand 43 attaches to the acceptor 35. Moreover, even if the non-specific ligand 44 is contained in the analysis sample solution 42, the ligand 44 disperses in the analysis sample solution 42 without attaching to the acceptor 35.

As shown in FIG. 4, the excitation light exited from the light source 37 enters the inclined plane of the prism 36, passes through the prism 36 and the transparent substrate 32, and then totally reflected at the surface of the transparent substrate 32, and again passes through the transparent substrate 32 and the prism 36, and exits to the outside from the inclined plane of the prism 36. The excitation light exited from the prism 36 is absorbed by the light absorbing plate 38 so as not to scatter and become a noise.

The evanescent light is generated at the surface of the transparent substrate 32 when the excitation light is totally reflects at the surface of the transparent substrate 32, where the evanescent light and each metal fine particle 33 locally plasmon resonate thereby generating a strong local electric field around the metal fine particles 33. According to the localized plasmon resonance, the electric field generated around the metal fine particles 33 is enclosed in a region of about the size of the metal fine particles 33. When the specific ligand 43 is contained in the analysis sample solution 42 and such specific ligand 43 is attached to the acceptor 35, the light emitting molecules modifying the ligand 43 is present within a local electric field region of the metal fine particles 33, and the luminescent light is generated from the light emitting molecule.

Therefore, determination on whether or not the specific ligand 43 is contained in the analysis sample solution 42 is made by observing the luminescent light emitted from the light emitting molecule through the lens 39 such as objective lens etc. The amount, concentration etc. of the specific ligand 43 attached to the acceptor 35 can be measured by measuring the emission intensity of the light emitting molecule, or by counting the luminescent spot formed by the light emitting molecule.

Figure 7:
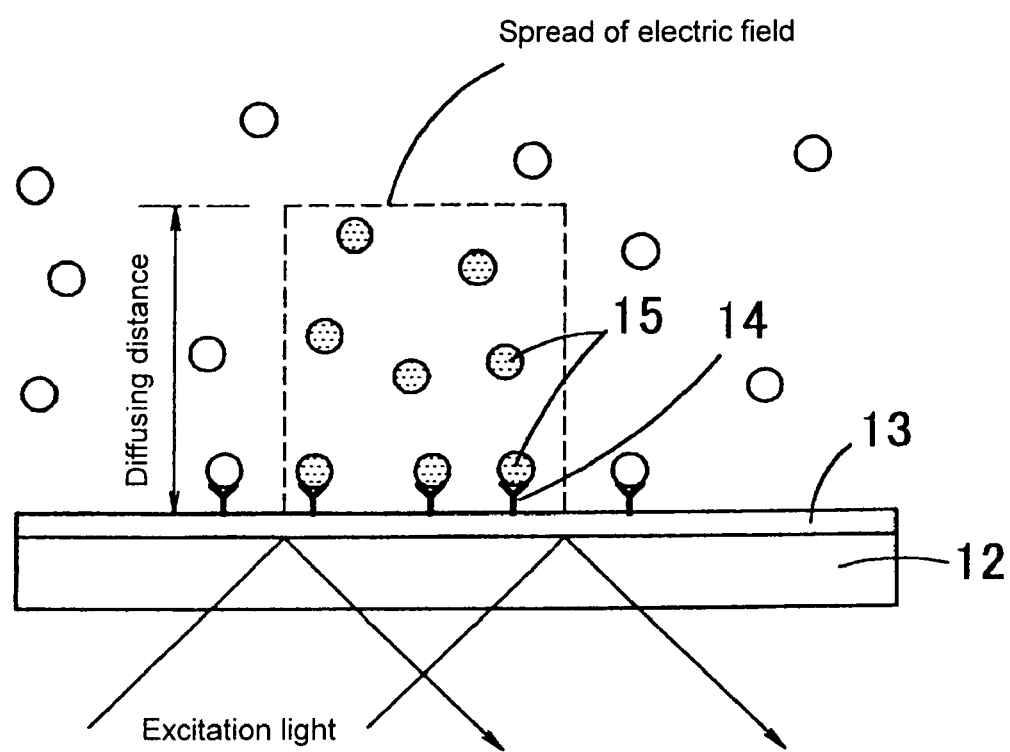
FIG. 7 is a view showing a range where a strong electric field is generated when a metal thin film is formed on the surface of the transparent substrate.
Figure 8:
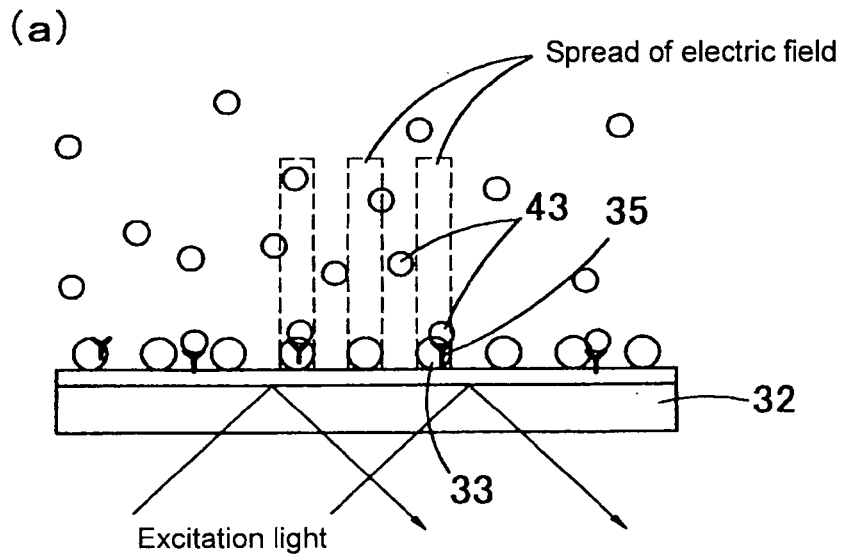
FIGS. 8(a), 8(b), and 8(c) are views for explaining the range where the strong electric field is generated in the localized plasmon resonance sensor of FIG. 4.
Figure 8:
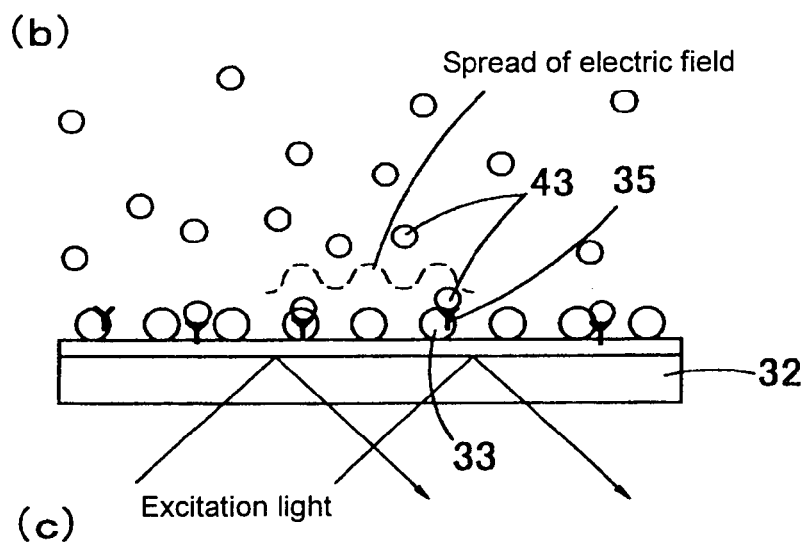
Figure 8:
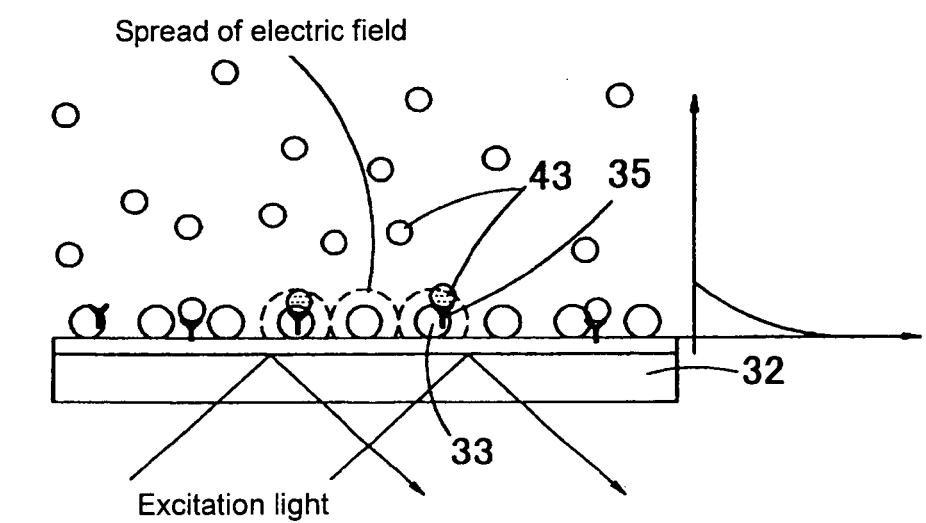

FIGS. 7 and 8 are views showing the effect of when the metal thin film 13 is formed on the surface of the transparent substrate 12 and of the localized plasmon resonance sensor 31 according to the present embodiment in comparison to each other. FIG. 7 shows the spread of the electric field of when the metal thin film 13 of even thickness is formed on the surface of the transparent substrate 12 (first conventional example), and FIGS. 8(*a*), 8(*b*), 8(*c*) describe the distribution of the electric field of when the metal fine particles 33 are fixed on the surface of the transparent substrate 32 (present embodiment). As well known, the electric field of the surface plasmon excited by the evanescent light spreads to about 200 to 300 nm (diffusing distance) from the surface of the transparent substrate 12 while exponentially attenuating, as shown in FIG. 7, for the case of the metal thin film 13. Thus, the electric field of the metal thin film 13 reaches even up to the ligand not attached to the acceptor 14, whereby even the light emitting molecules modifying the ligand 15 at a relatively far distance from the acceptor 14 such as the ligand 15 dotted in FIG. 7 emit light and become a noise, thereby lowering the measurement accuracy.

On the other hand, when the metal fine particles 33 are formed on the surface of the transparent substrate 32 as in the present embodiment, in principle, a strong electric field is generated only at the position of the metal fine particles 33, as shown in FIG. 8(*a*). However, since this electric field is averaged, as shown in FIG. 8(*b*), the electric field at the position of the metal fine particles 33 becomes weak. In particular, in the case of the metal fine particles 33, the electric field is enclosed in the vicinity of the metal fine particles 33, as shown in FIG. 8(*c*). According to the research related to the localized plasmon resonance of when the light is irradiated perpendicular to the metal fine particles, the electric field is known to be enclosed in the region of about the size of the metal fine particles. The light emitting molecule modifying the specific ligand 43 attached to the acceptor 35 such as the light emitting molecule modifying the ligand 43 dotted in FIG. 8(*c*) emits light due to the localized electric field. However, the specific ligand 43 not attached to the acceptor 35 or the non-specific ligand 44 do not emit light and thus the noise is less likely to be produced, and the presence or the amount of the specific ligand 43 attached to the acceptor 35 can be measured at satisfactory accuracy.

In the conventional localized plasmon resonance (see second conventional example), the light is irradiated perpendicular to the metal fine particles to have the light (traveling wave) and the metal fine particles locally plasmon resonate directly, but only the light having a light flux cross section equal to the cross sectional area of the metal fine particles couples with the metal fine particles in this localized plasmon resonance method, and thus the bonding efficiency of the light and the metal fine particles is low. Therefore, in the present embodiment, the feature of the present example also includes enhancing the bonding efficiency of the light and the metal fine particles by coupling the evanescent light and the metal fine particles so as to locally plasmon resonate.

Figure 9:
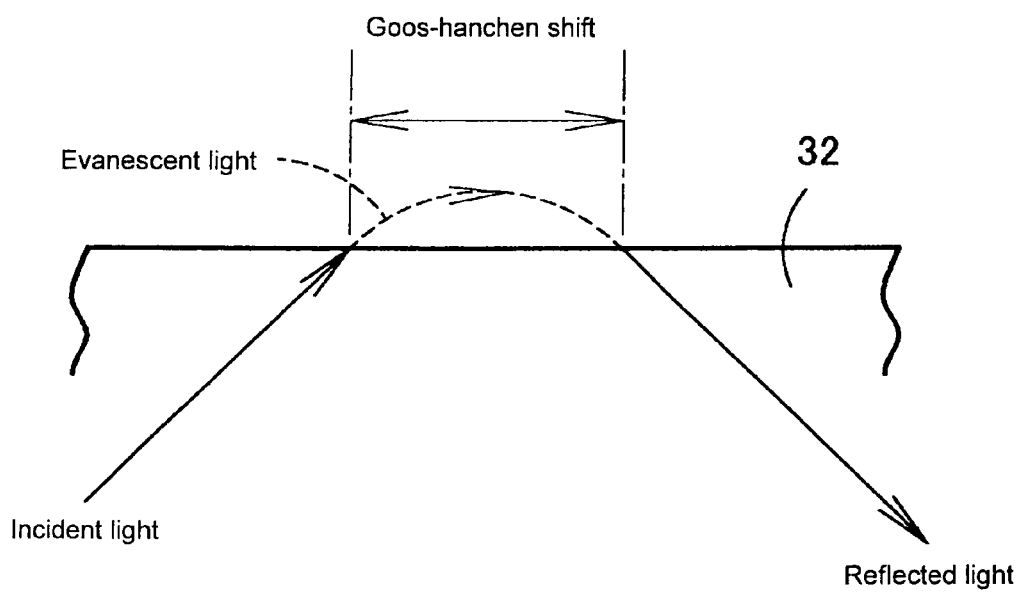
FIG. 9 is a view explaining the Goos-Hanchen effect.
Figure 10:
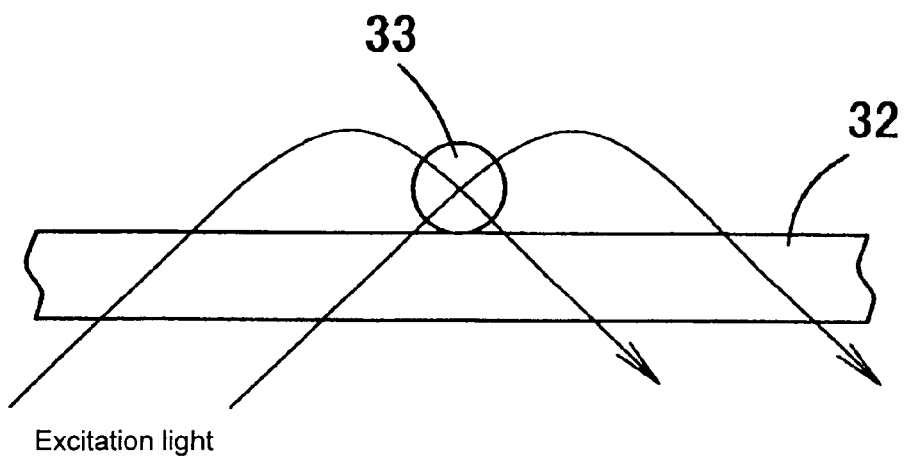
FIG. 10 is a view describing the bond between the evanescent light and the metal fine particles.

In the present embodiment, the excitation light is irradiated diagonally to the transparent substrate 32, and the excitation light is totally reflected at the surface of the transparent substrate 22. When the light is totally reflected at the interface, a jump occurs between the incident point and the exit point of the reflected light at the interface, as shown in FIG. 9. This phenomenon is known as the Goos-Hanchen effect (e.g., Jackson electromagnetics third edition (upper volume), Yoshioka Publishing Company, pps. 426-429), and the jump is referred to as the Goos-Hanchen shift. As shown with a broken line in FIG. 9, the light totally reflected at the interface diffuses outward from the interface and is enclosed in the vicinity of the interface. This is the evanescent light.

As in the present embodiment, when the light is irradiated diagonally to the transparent substrate 32 fixed with the metal fine particles 33 and then totally reflected, the excitation light from the transparent substrate 32 towards the metal fine particles 33 side excites the metal fine particles 33, and the excitation light returning from the metal fine particles 33 side towards the transparent substrate 32 also excites the metal fine particles 33, whereby the bonding efficiency of the metal fine particles 33 and the excitation light enhances compared to the perpendicular irradiation.

This can be explained in a different manner as described below. As shown in FIG. 9, the evanescent light moves parallel to the interface in the vicinity of the interface. Therefore, when the light having a light flux cross section greater than the cross section of the metal fine particles diagonally enters the interface and is totally reflected, the light of such large light flux cross section is enclosed in the vicinity of the interface as the evanescent light and moves parallel to the interface. When the evanescent light impinges the metal fine particles and couples to the same, the light of light flux cross section greater than the cross section of the metal fine particles effectively couples to the metal fine particles, and the bonding efficiency between the light and the metal fine particles enhances.

Therefore, according to the present embodiment, by enhancing the bonding efficiency of the metal fine particles 33 and the excitation light, a stronger electric field is generated in the vicinity of the metal fine particles 33, the light emitting molecule emits light more strongly, and the S/N ratio of the signal is enhanced.

However, although the bond between the light and the metal fine particles becomes large when the Goos-Hanchen shift becomes large, the diffusing distance of the evanescent light also increases, and thus the desired conditions such as the wavelength of the excitation light, the index of refraction of the transparent substrate 32 etc. exist, but are experimentally determined.

Figure 11:
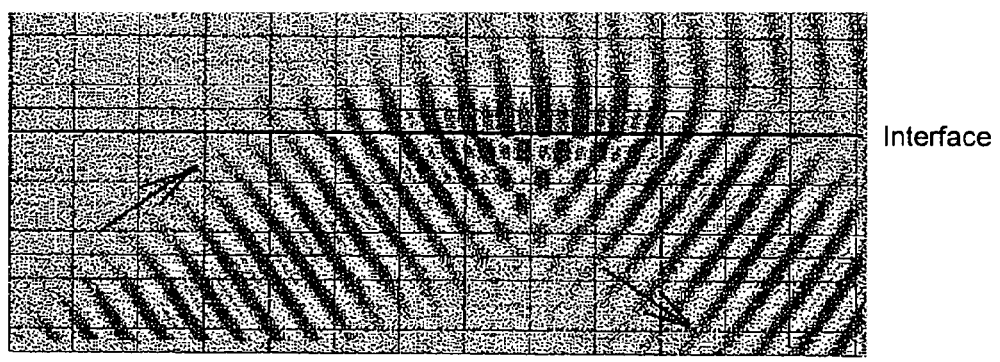
FIG. 11 is a view showing the distribution of the electric field when the light is totally reflected at the interface of the transparent substrate.
Figure 12:
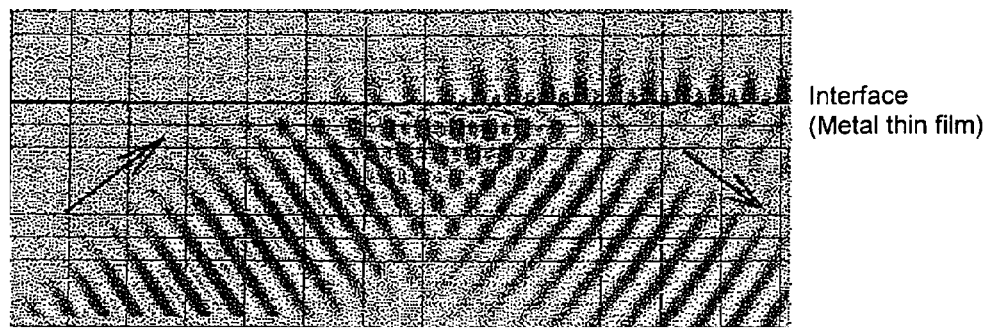
FIG. 12 is a view showing the distribution of the electric field when the light is totally reflected at the interface of the transparent substrate formed with the metal thin film on the surface.
Figure 13:
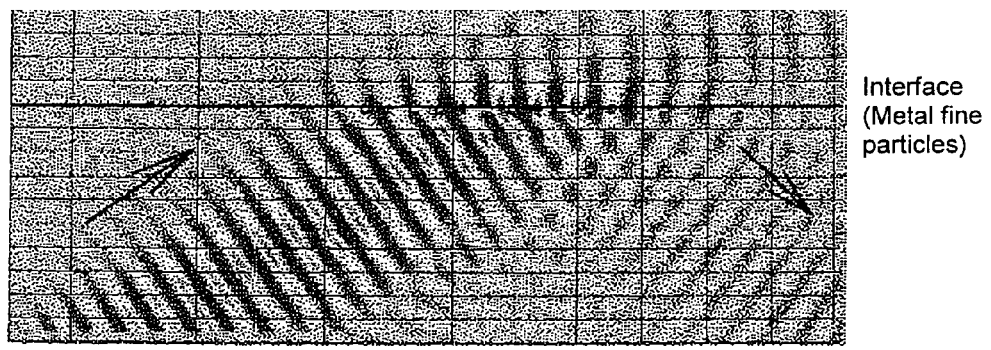
FIG. 13 is a view showing the distribution of the electric field of when the light is totally reflected at the interface of the transparent substrate formed with the metal fine particles on the surface.

FIGS. 11 and 12 show the result of simulating the situations in which the light is totally reflected at the interface of the transparent substrate in a cross section perpendicular to the transparent substrate, where the degree of grayscale represents the intensity of the electric field. FIG. 11 shows the simulation in which water (index of refraction 1.33) is simply contacted to the surface of the glass substrate (transparent substrate) having an index of refraction of 1.732, and the metal thin film and the metal fine particles are not arranged. In this case, the electric field intensity of the reflected wave is relatively high and the evanescent light diffuses to about 600 nm. FIG. 12 shows the simulation in which the Au thin film (metal thin film) having a thickness of 50 nm is formed on the surface of the glass substrate having an index of refraction of 1.732 and the water is contacted thereto. In this case, no significant difference is found with when the metal thin film is not arranged, and the evanescent light diffuses to about 200 to 300 nm. FIG. 13 shows the simulation in which the Ag particles having a diameter of 600 nm are arranged on the surface of the glass substrate (transparent substrate) having an index of refraction of 1.732 at an interval of 180 nm, and the water is contacted to the surface. In this case, the light is absorbed by the Ag particles and thus the electric field intensity of the reflected light is weaker, and the electric field is enclosed in the vicinity of the Ag particles. The electric field in the vicinity of the Ag particles increases by greater than or equal to ten times compare to when the metal fine particles and the metal thin film are not arranged. According to this simulation, the electric field is enclosed in a region narrower than in the metal thin film, and large electric field intensity is obtained by acting the evanescent light on the metal fine particles.

Figure 14:
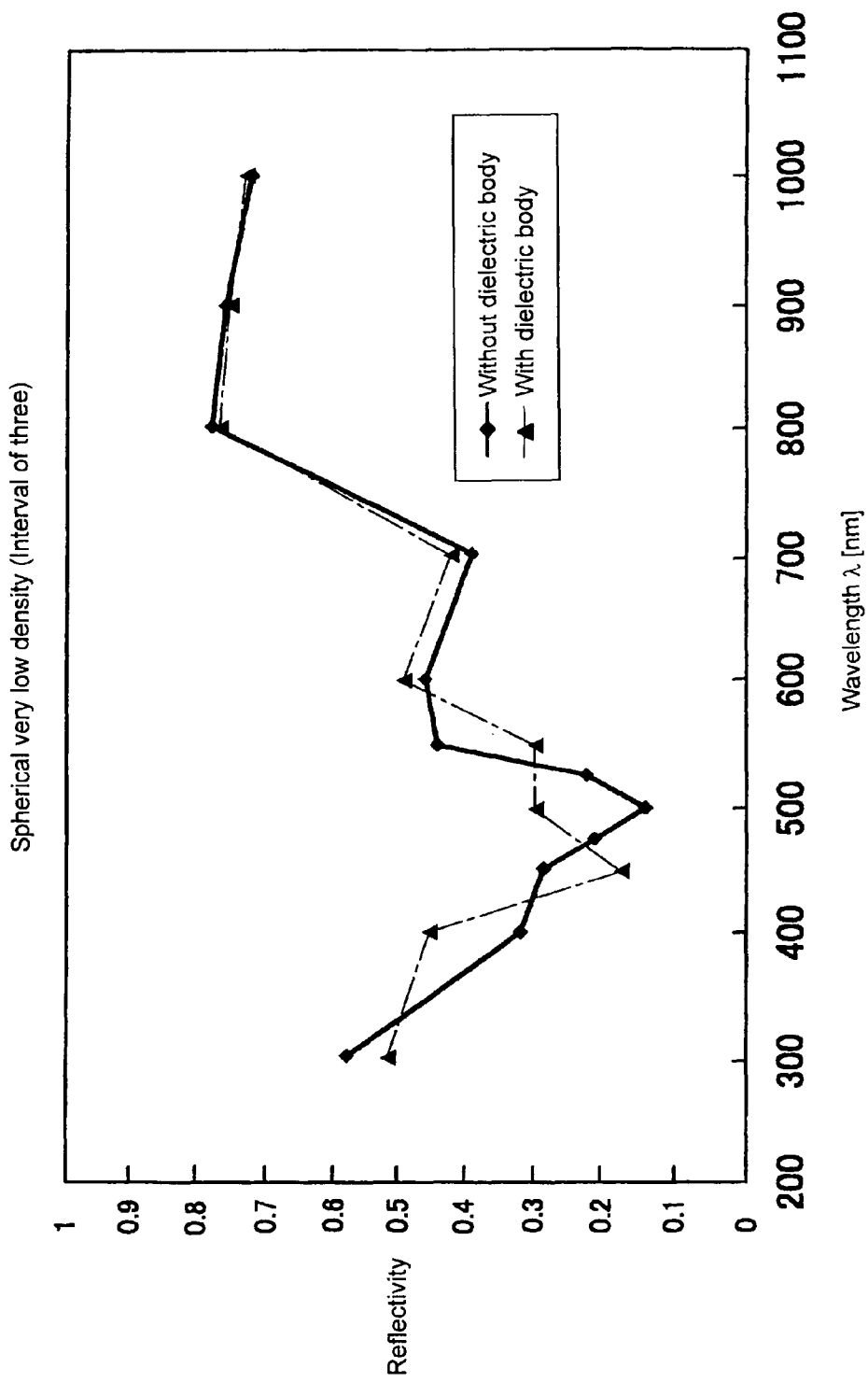
FIG. 14 is a view showing the relationship between the wavelength λ of the incident light and the reflectivity at the interface in the localized resonance sensor as shown in FIG. 4 arranged with the metal fine particles on the transparent substrate.

FIG. 14 shows the result of the simulation in which the relationship between the wavelength λ of the incident light and the reflectivity at the interface is obtained for those formed with Ag particles on the surface of the glass substrate at an interval of three times the diameter of the metal fine particles and at a coverage of 25%, under the same condition as the simulation of FIG. 13. FIG. 14 shows a case of when a dielectric film having a thickness of 20 to 30 nm and having an index of refraction of 1.42 is formed on the substrate from above the metal fine particles, and a case of when the dielectric film is not formed, where the reflectivity increases when the dielectric body is arranged and the index of refraction increases. Furthermore, according to such simulation, it is found that the light absorptivity (about 15 to 20% reflectivity) of about 80 to 85% is obtained (including influence of diffraction and the like), and the bonding of the light and the metal fine particles is enhanced.

Figure 15:
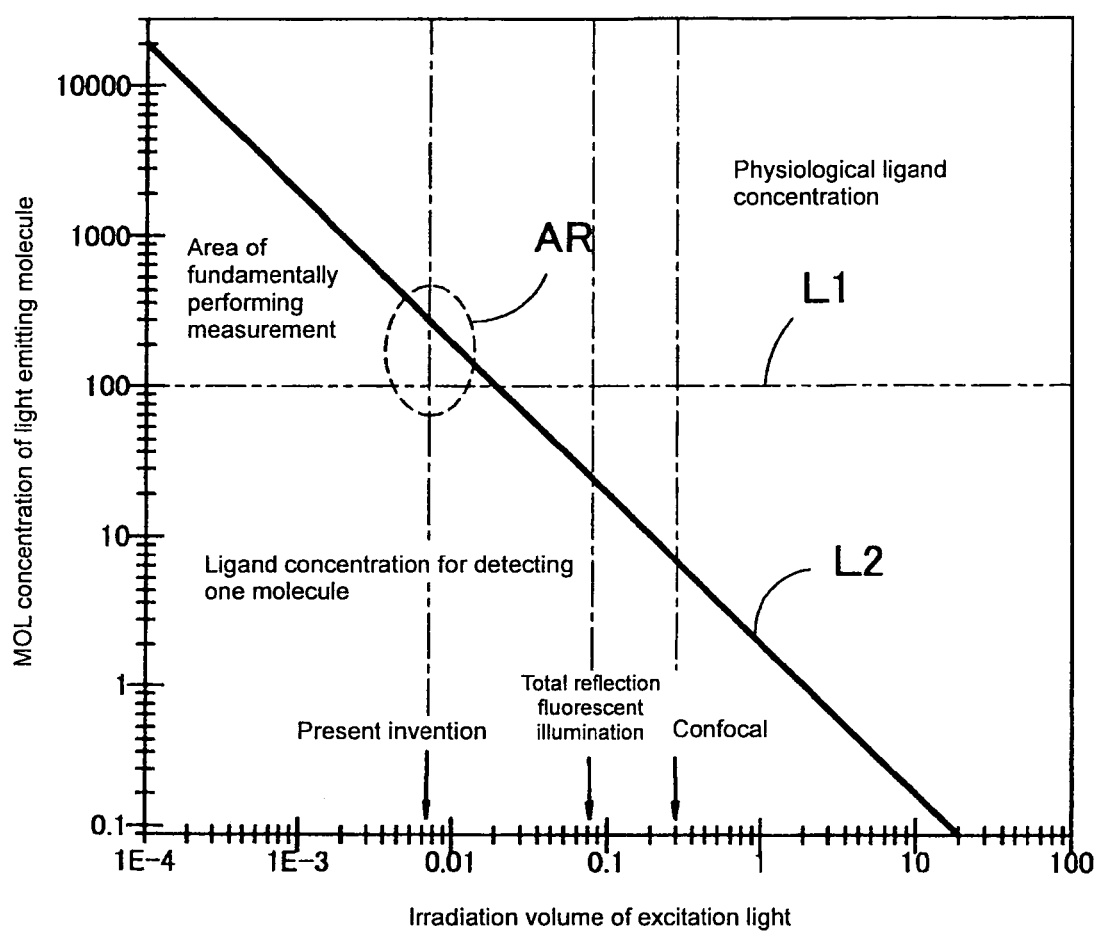
FIG. 15 is a view showing the relationship between the irradiation volume of the excitation light, the mol concentration of the light emitting molecule, and the ligand concentration for detecting one molecule.
Figure 16:
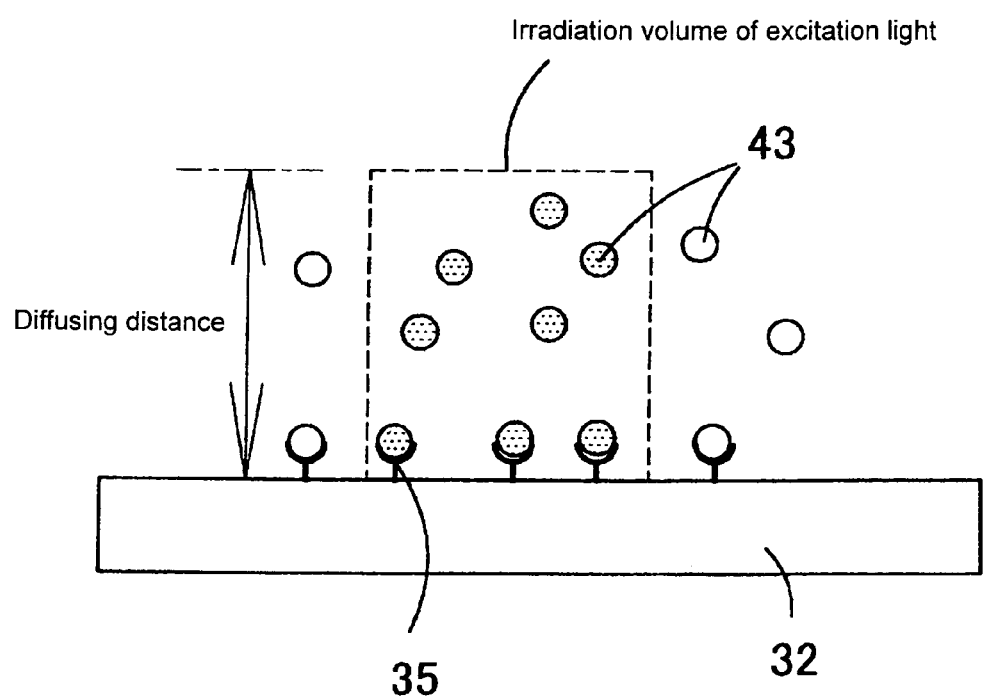
FIG. 16 is a view describing the meaning of irradiation volume.

FIG. 15 is a view showing the relationship between the irradiation volume of the excitation light, the mol concentration of the light emitting molecule, and the ligand concentration for detecting one molecule, where the horizontal axis shows the irradiation volume [fL=$10^{-15}$ liter] of the excitation light and the vertical axis shows the mol concentration [nM=nanomol/liter] of the light emitting molecule. The irradiation volume is a volume of a cube where the bottom surface is a Predetermined unit area, and the height is the distance (diffusing distance) affected by the electric field, and the light emitting molecules in the cube of the irradiation volume is excited to emit light, as shown in FIG. 16. In FIG. 15, the region above line L1 shows the region of the physiological ligand concentration contained in body fluid and the like, and the region on the lower left of line L2 shows the region where the ligand of one molecule can be detected. Therefore, in order to detect the ligand of one molecule with the analysis sample solution of the physiological ligand concentration of body fluid and the like as the target, the measurement must be performed in a triangular region positioned above line L1 and on the lower left of line L2, as shown in FIG. 15.

The irradiation volume of the excitation light is about 0.2 fL in the confocal microscope, and the irradiation volume is about 0.08 fL when the acceptor is arranged on the metal thin film. Thus, the region where one molecule can be detected with the physiological ligand concentration does not exist on the vertical line indicating the irradiation volume. The irradiation volume of the excitation light becomes about 0.008 fL in the localized resonance sensor 31 of the present embodiment where the metal fine particles 33 and the acceptor 35 are fixed on the transparent substrate 32, on the other hand, and thus the ligand of one molecule can be detected around the region AR of FIG. 15 with the analysis sample solution of physiological ligand concentration as the target.

In the above embodiment, the spherical metal fine particle 33 is used as the convex part of the metal layer, but the metal fine particle 33 may be an ellipse. Alternatively, the metal fine particle 33 may be a part of a sphere or an ellipse as shown in FIG. 17(*a*).

Figure 17:
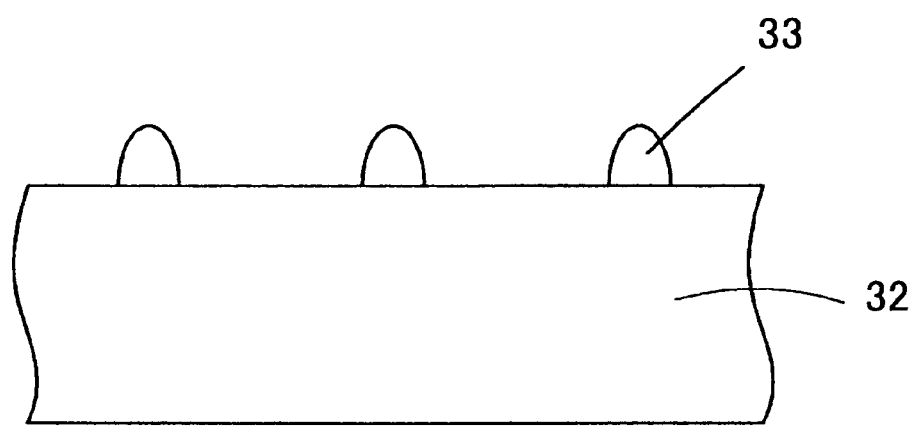
FIG. 17(a) is a view showing a different shape of the metal fine particles.
FIG. 17(b) is a view showing convex parts formed with the metal fine particles on the metal thin film.
Figure 17:
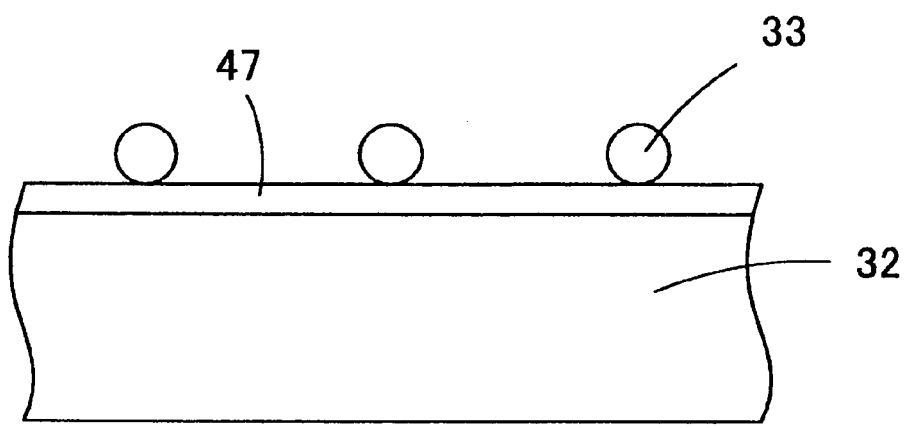

The metal fine particles 33 are formed directly on the transparent substrate 32 in the above embodiment, but the metal thin film 47 may be formed on the transparent substrate 32 and then the metal fine particles 33 may be arranged on the metal thin film 47, as shown in FIG. 17(*b*). Alternatively, the metal fine particles 33 may be fixed on the transparent substrate 32, and then the surface of the transparent substrate 32 may be covered by the metal thin film 47 from above the metal fine particles 33, as shown in FIG. 18(*a*).

Figure 18:
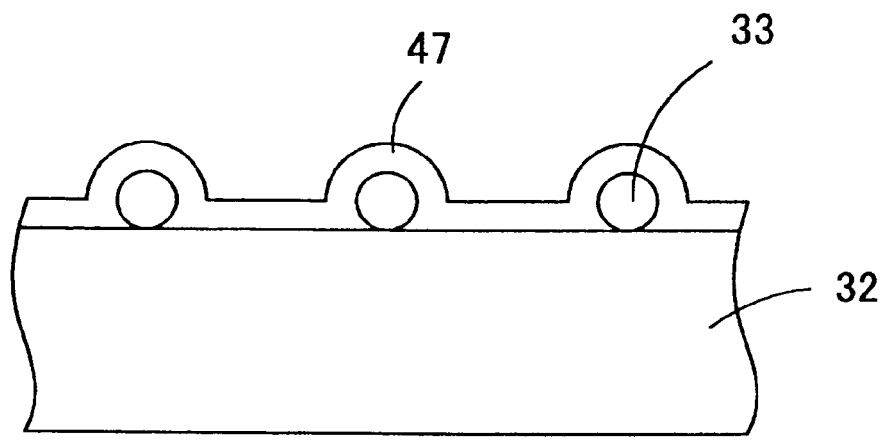
FIG. 18(a) is a view where the metal fine particles on the transparent substrate are covered with the metal thin film to form the convex part.
FIG. 18(b) is a view where the concave part is formed in the metal thin film.
Figure 18:
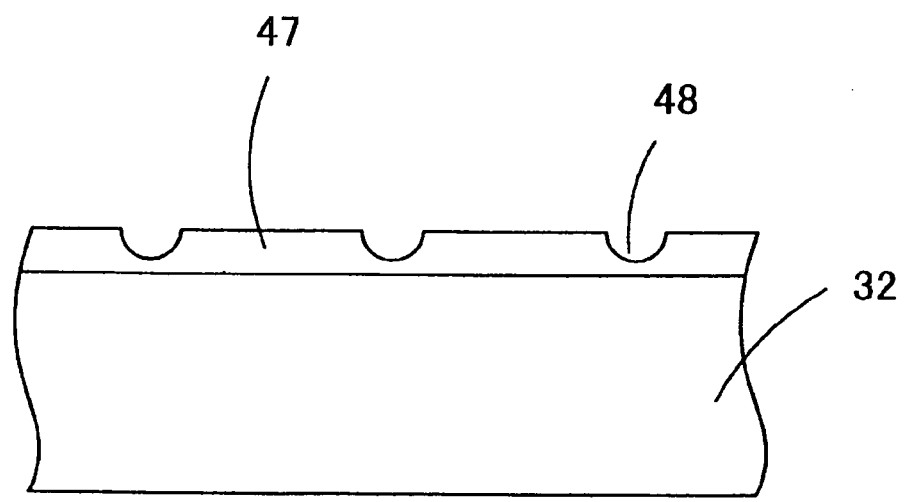
Figure 19:
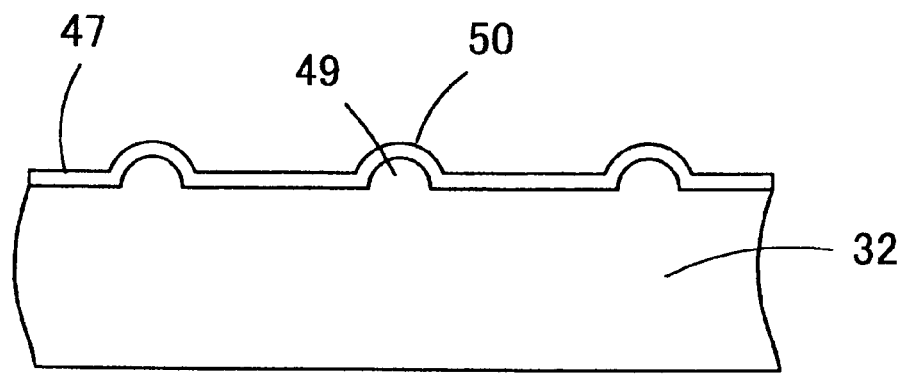
FIG. 19(a) is a view where the surface of the transparent substrate formed with the projection is covered with the metal thin film to form the convex part.
FIG. 19(b) is a view where the surface of the transparent substrate formed with the depression part is covered with the metal thin film to form the concave part.
Figure 19:
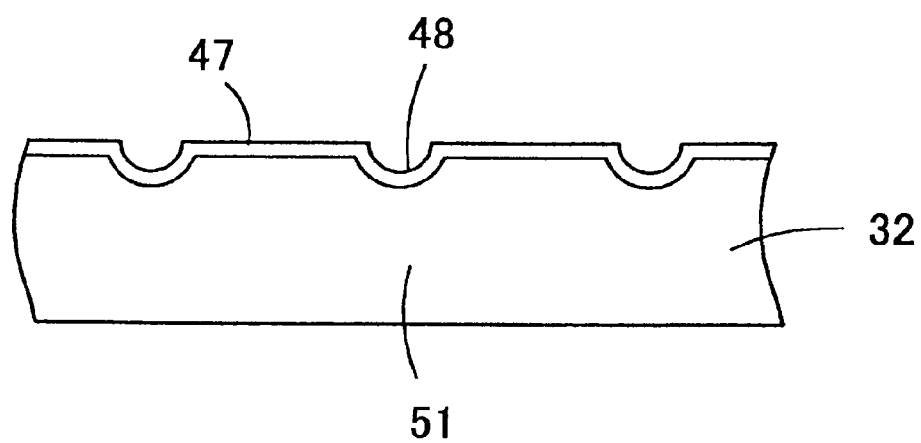

In the variant shown in FIG. 18(*b*), a depression is partially formed in the metal thin film 47 formed on the surface of the transparent substrate 32 as the concave part 48 of the metal layer. Alternatively, a projection 49 may be arranged on the surface of the transparent substrate 32 and the surface may be covered with the metal thin film 47 to form a convex part 50 of the metal layer, as shown in FIG. 19(*a*), or a depression part 51 may be formed in the surface of the transparent substrate 32 and the relevant surface may be covered with the metal thin film 47 to form the concave part 48 of the metal layer, as shown in FIG. 19(*b*). As can be easily predicted, the efficiency lowers compared to the isolated metal fine particles if the convex parts or the concave parts are connected.

Figure 20:
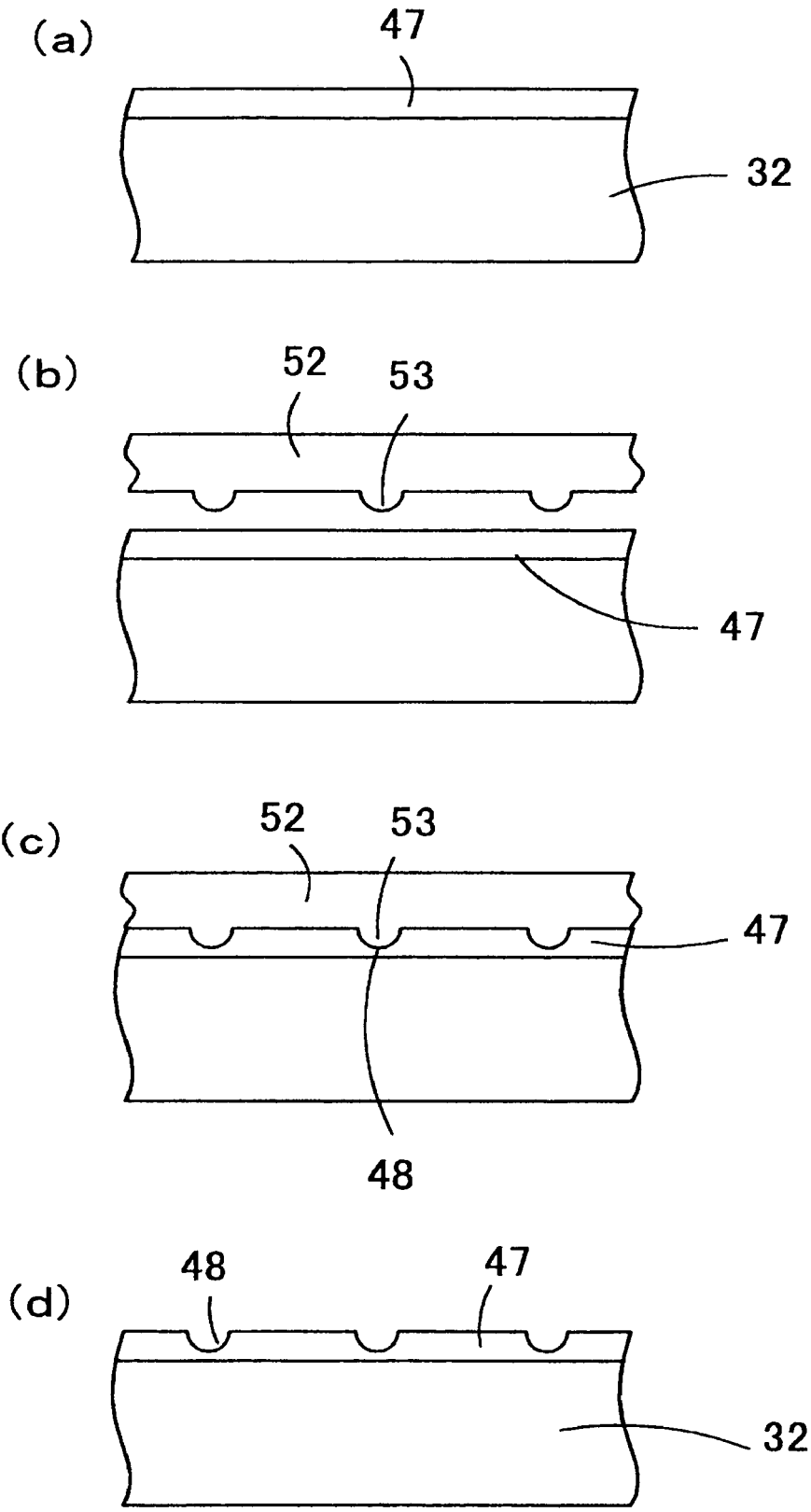
FIGS. 20(a) to 20(d) are schematic views showing the steps of forming the concave part with a stamper.

Various convex parts or concave parts, projections 49, depression parts 51 etc. can be formed through embossing using a stamper. For example, FIGS. 20(*a*) to 20(*d*) describe a case of forming the concave part 48 as in FIG. 18(*b*) with the stamper. The metal thin film 47 is deposited on the surface of the transparent substrate 32 (FIG. 20(*a*)), and then pressed down with the stamper 52 from above the metal thin film 47 (FIG. 20(*b*)). Since formation projections 53 are arranged on the lower surface of the stamper 52, the concave parts 48 are transferred to the surface of the metal thin film 47 with the forming projection 53 when the metal thin film 47 is pressed with the stamper 52 (FIG. 20(*c*)). After releasing the stamper 52, the concave parts 48 of nano scale are formed on the surface of the metal thin film 47.

Figure 21:
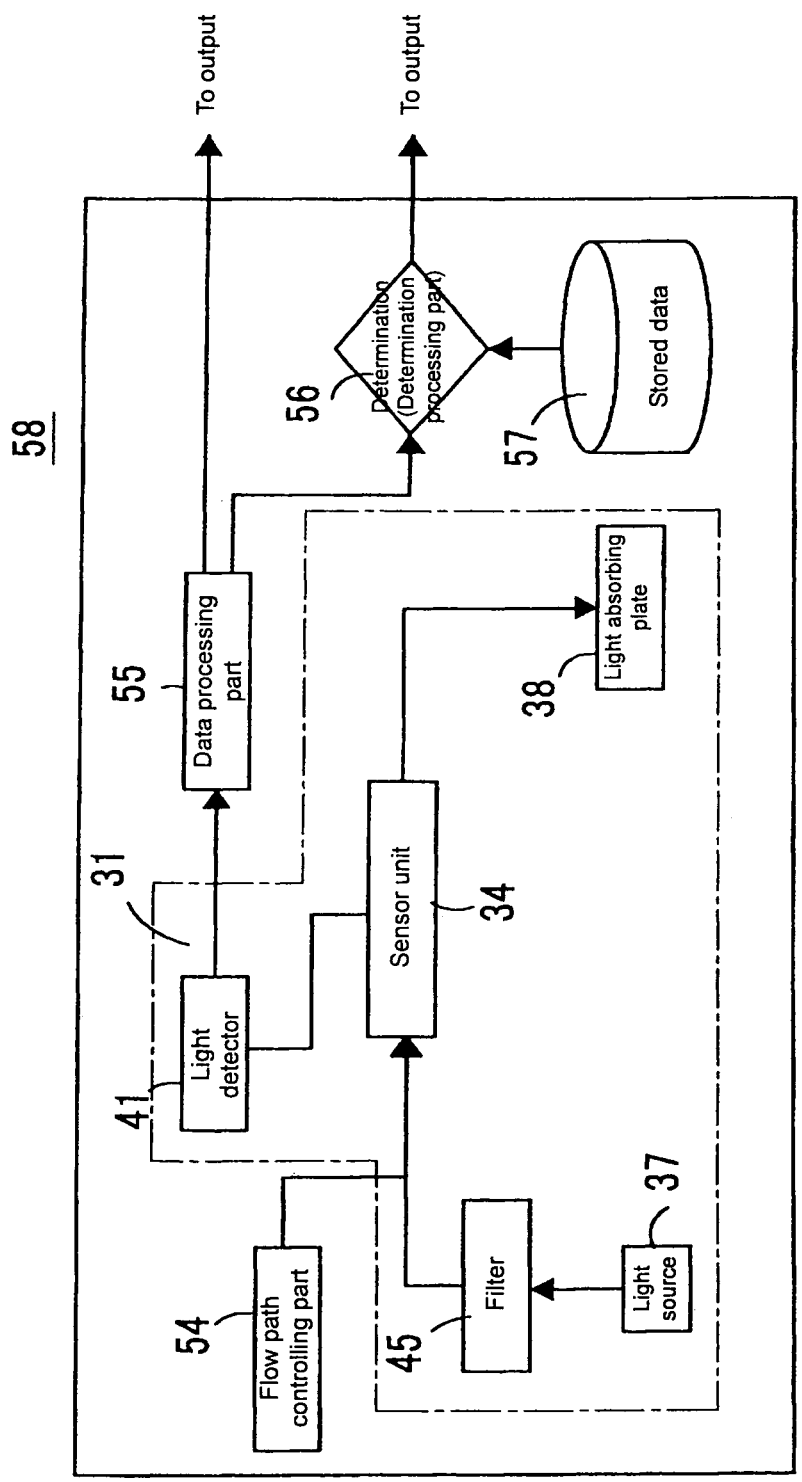
FIG. 21 is a block diagram showing the configuration of an examining device using the localized plasmon resonance sensor of the present invention.
Figure 22:
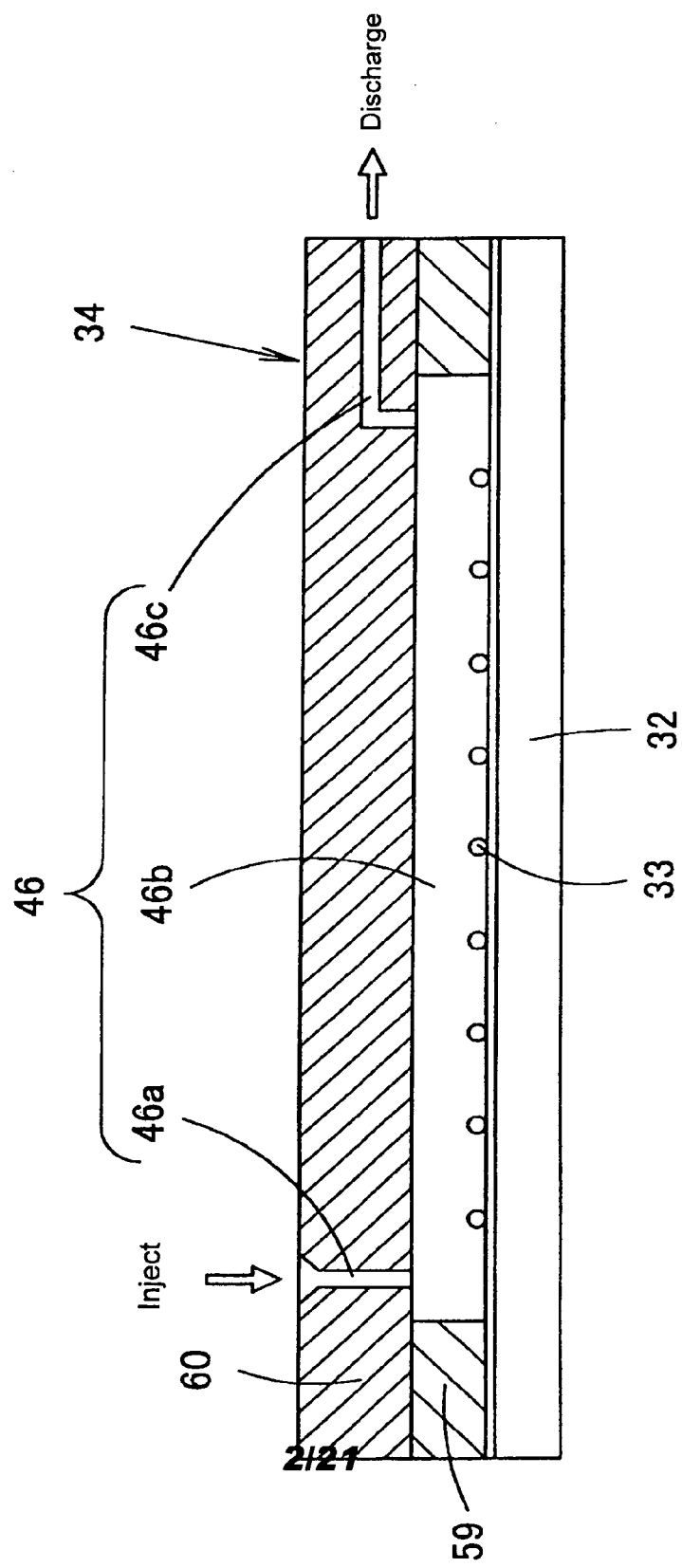
FIG. 22 is a cross sectional view showing the sensor unit of the examining device shown in FIG. 21.
Figure 23:
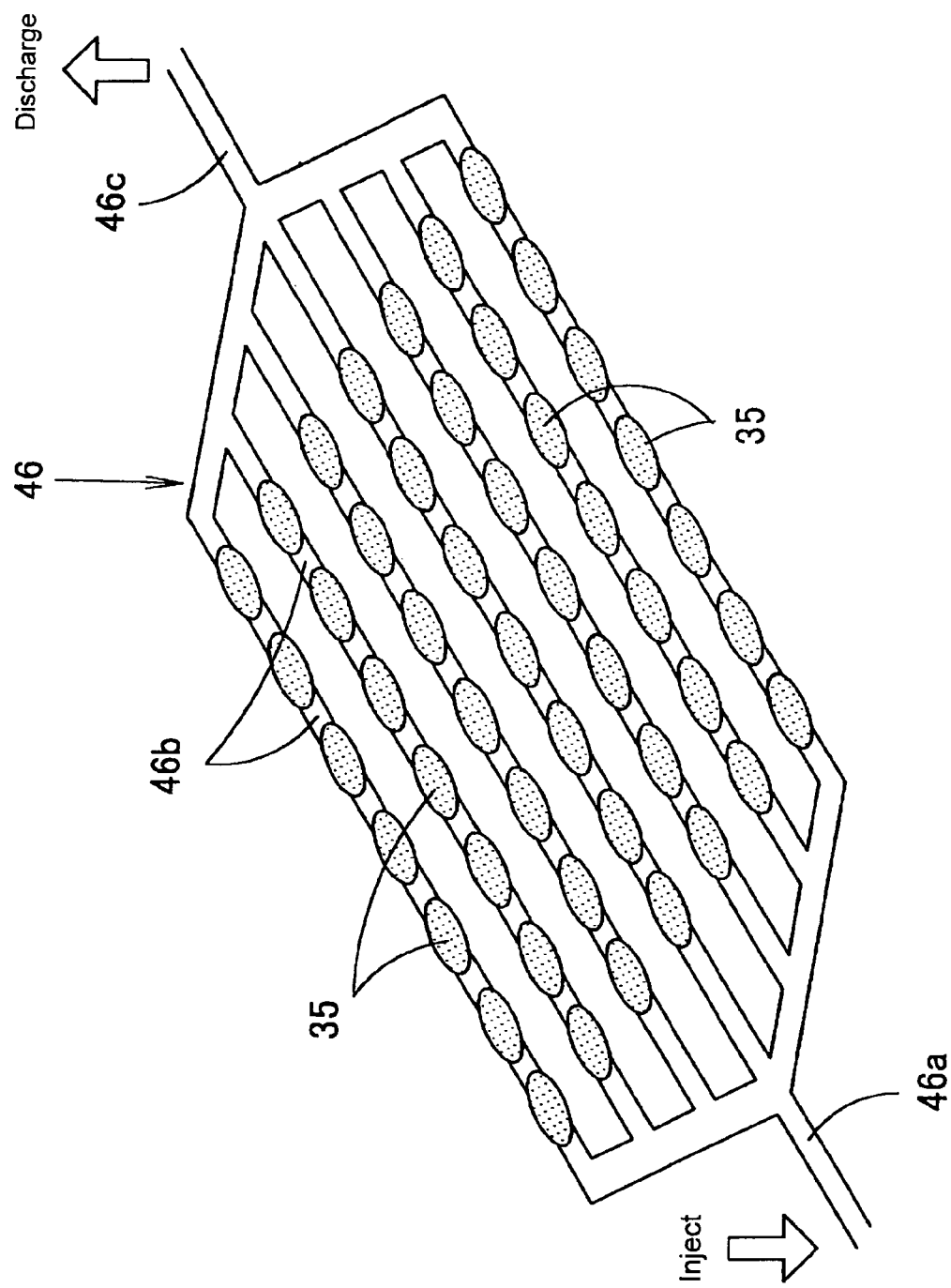
FIG. 23 is a schematic perspective view showing the flow path inside the examining device shown in FIG. 22.

The configuration of an examining device 58 using the localized plasmon resonance sensor of the present invention will now be described. FIG. 21 is a block diagram showing the configuration of the examining device 58, FIG. 22 is a cross sectional view of the sensor unit 34, and FIG. 23 is a schematic perspective view showing the flow path where the analyte inside the sensor unit 34 flows. The entire configuration of the localized plasmon resonance sensor 31 is as described above. In the sensor unit 34, a great number of metal fine particles 33 are fixed on the surface of the substrate 32 made of glass substrate and the like to form the metal layer. A predetermined type of acceptor is immobilized on the surface of the transparent substrate 32 and the metal fine particles 33 as the molecule recognition functional substance. A cover 60 is superimposed on the substrate 32 by way of the spacer 59, and the flow path 46 as shown in FIG. 23 is formed in the spacer 59 and the cover 60. An injection path 46a and a discharge path 46c are respectively formed at both ends of the cover 60, and a plurality of branched flow paths 46b are formed in the spacer 59 between the cover 60 and the substrate 32. In other words, the flow path 46 has one injection path 46a branched into pluralities to become branched passages 46b separated from each other, which again merges at the other end of each branched passage 46b to become one discharge path 46c. A Predetermined acceptor 35 is immobilized in each branched flow path 46b.

When the analysis sample solution is dropped into the injection path 46a, and the analysis sample solution is flowed through the flow path 46 by way of pump, electroosmotic flow etc., the analysis sample solution is divided and flowed into each branched flow path 46b and then again collected at the discharge path 46c and discharged to the outside. When the analysis sample solution flows through each branched flow path 46b, the specific ligand bonds with the acceptor 35, and the others pass through the branched passage 46b to the discharge path 46c.

The flow path controlling part 54 adjusts the supply speed of the analysis sample solution to supply to the flow path of the sensor unit 34, and performs the control so that the analysis sample solution flows at an even speed. The data processing part 55 converts the measurement data acquired at the light detector 41 to the data format that can be handled at the determination processing part 56, and sends the result to the determination processing part 56. The determination processing part 56 reads the stored determination data from the storage device 57 such as a hard disc, compares the processing data received from the data processing part 55 and the determination data, and analyzes the presence of the specific ligand, the concentration of the specific ligand and the like in the analysis sample solution according to a predetermined algorithm. The output data of the data processing part 55 and the determination result of the determination processing part 56 are output to the output terminal and the like.

The presence, amount, intermolecular interaction, bonding force, equilibrium constant of the ligand in the analysis sample solution can be evaluated by measuring the evanescent light from the sensor unit 34 using the examining device 58. For example, when flowing the sample DNA marked with fluorescent dye and the like on the transparent substrate immobilized with the probe DNA at high density, the DNA complementary to each other bond with each other. Thus, the presence or the extent of the interaction between each probe DNA and the sample DNA are evaluated by detecting the signal at each position on the transparent substrate.

Furthermore, since the flow path 46 is branched into a plurality of branched flow paths 46b, as shown in FIG. 13, a specific ligand different for each branched flow path 46b can be examined by immobilizing different types of acceptor for each branched flow path 46b. Thus, a plurality of different examinations can be simultaneously performed with one drop of analysis sample solution.

The object to be examined includes protein, sugar chain, cells and the like in addition to DNA. Determination of gene sequence, check for the presence of biomolecules such as specific gene, protein, sugar chain etc., measurement of appearance level of a specific biomolecules, analysis of intermolecular interaction and the like become possible according to the relevant method. Furthermore, analysis of the original active function of the living body becomes possible since the behavior of the biomolecules under high concentration, that is, under bio-concentration can be detected using the present invention.

Other applications of the localized plasmon resonance sensor or the examining device according to the present invention includes (i) analysis of SNP (single nucleotide polymorphisms), (ii) check for path or state of metabolism, absorption, excretion of the substance administered to an experimental mouse, (iii) ion concentration measurement in the cell, (iv) identification or function analysis of protein etc.

Using the analysis method according to the present invention, antigen or antibody can be detected from saliva or blood to determine the health condition of an individual, to read the gene information of each individual or to perform medical diagnosis at the gene level. For example, the health condition of the individual can be determined to perform checkup by dropping saliva or blood in the inserting part of the flow path of the present system and detecting antigen such as cancer cell, virus and the like, antibody against virus and the like. Therefore, as a result of using the analysis method according to the present invention, the possibility of side effect of the medicine can be researched, the fear of false diagnosis can be reduced as much as possible and a sophisticated medical diagnosis can be realized.

Other applications include building a high precision security system by reading information of a specific gene or biomolecules etc. present in each individual, and further, use in detection and the like of fine particles contained in food, in environment, that is, in air or in water.

It should be apparent to those skilled in the art that the present invention may be embodied in many other specific forms without departing from the spirit or scope of the invention. Therefore, the present invention is not to be limited to the details given herein, but may be modified within the scope and equivalence of the appended claims.

The invention claimed is:

1. A localized plasmon resonance sensor comprising:
   a sensor unit having a metal layer with a plurality of convex parts or concave parts formed by fixing metal particles having a diameter of between 10 and 30 nm at an interval of greater than or equal to two times and less than or equal to four times the diameter in average from each other on a surface of a transparent substrate, and molecule recognition functional substance for attaching a specific analyte immobilized on the substrate or the metal layer; and
   a light emitting module configured facing a back surface of the transparent substrate, such that a light emitted by the light emitting module reaches the metal layer passing through the transparent substrate;
   wherein the surface arranged with the metal layer and the molecule recognition functional substances of the sensor unit is contacted to an analysis sample solution containing analyte modified with the light emitting molecule;
   an evanescent light generated at the surface of the substrate by an excitation light irradiated at an incident angle totally reflected at the surface of the substrate onto the other surface of the sensor unit and the metal layer Plasmon resonate to locally intensify an electric field around the metal layer; and
   presence or concentration of the analyte attached to the molecule recognition functional substance is measured by detecting a luminescent light excited and emitted from the light emitting molecule of the analyte attached to the molecule recognition functional substance among the analytes with the electric field.

2. The localized plasmon resonance sensor according to claim 1, wherein a prism is arranged closely attached to the back surface of the substrate.

3. The localized plasmon resonance sensor according to claim 1, wherein the height and the width of the convex part or the concave part are both less than or equal to 150 nm.

4. The localized plasmon resonance sensor according to claim 1, wherein a shape of a metal fine particle is a sphere, an elliptical sphere, or one part of the sphere or the elliptical sphere.

5. The localized plasmon resonance sensor according to claim 1, wherein the metal layer comprises Au or Ag.

6. An examining device comprising a localized plasmon resonance sensor according to claim 1, and a means for analyzing an analysis sample solution based on output data of the sensor.

7. A localized plasmon resonance sensor comprising:
a sensor unit having a metal layer with a plurality of convex parts or concave parts formed by fixing metal particles having a diameter of between 10 and 30 nm at an interval of greater than or equal to two times and less than or equal to four times the diameter in average from each other on a surface of a transparent substrate, and molecule recognition functional substance for attaching a specific analyte immobilized on the substrate or the metal layer;
wherein the surface arranged with the metal layer and the molecule recognition functional substances of the sensor unit is contacted to an analysis sample solution containing analyte modified with a light emitting molecule;
an evanescent light generated at the surface of the substrate by an excitation light irradiated at an incident angle totally reflected at the surface of the substrate onto the other surface of the sensor unit and the metal layer Plasmon resonate to locally intensify an electric field around the metal layer; and
presence or concentration of the analyte attached to the molecule recognition functional substance is measured by detecting a luminescent light excited and emitted from the light emitting molecule of the analyte attached to the molecule recognition functional substance among the analytes with the electric field; and
wherein a light detector for detecting the luminescent light is arranged by way of a lens on the side facing the surface arranged with the metal layer and the molecule recognition functional substances of the sensor unit.

8. A localized plasmon resonance sensor comprising:
a sensor unit having a metal layer with a plurality of convex parts or concave parts formed by fixing metal particles having a diameter of between 10 and 30 nm at an interval of greater than or equal to two times and less than or equal to four times the diameter in average from each other on a surface of a transparent substrate, and molecule recognition functional substance for attaching a specific analyte immobilized on the substrate or the metal layer;
wherein the surface arranged with the metal layer and the molecule recognition functional substances of the sensor unit is contacted to an analysis sample solution containing analyte modified with a light emitting molecule;
an evanescent light generated at the surface of the substrate by an excitation light irradiated at an incident angle totally reflected at the surface of the substrate onto the other surface of the sensor unit and the metal layer Plasmon resonate to locally intensify an electric field around the metal layer; and
presence or concentration of the analyte attached to the molecule recognition functional substance is measured by detecting a luminescent light excited and emitted from the light emitting molecule of the analyte attached to the molecule recognition functional substance among the analytes with the electric field; and
wherein the emission wavelength of the light emitting molecule and the wavelength of the excitation light are different.

9. The localized plasmon resonance sensor according to claim 8, wherein a cut filter for shielding the excitation light is arranged in front of the light detector.

10. A localized plasmon resonance sensor comprising:
a sensor unit having a metal layer with a plurality of convex parts or concave parts formed by fixing metal particles having a diameter of between 10 and 30 nm at an interval of greater than or equal to two times and less than or equal to four times the diameter in average from each other on a surface of a transparent substrate, and molecule recognition functional substance for attaching a specific analyte immobilized on the substrate or the metal layer;
wherein the surface arranged with the metal layer and the molecule recognition functional substances of the sensor unit is contacted to an analysis sample solution containing analyte modified with a light emitting molecule;
an evanescent light generated at the surface of the substrate by an excitation light irradiated at an incident angle totally reflected at the surface of the substrate onto the other surface of the sensor unit and the metal layer Plasmon resonate to locally intensify an electric field around the metal layer; and
presence or concentration of the analyte attached to the molecule recognition functional substance is measured by detecting a luminescent light excited and emitted from the light emitting molecule of the analyte attached to the molecule recognition functional substance among the analytes with the electric field; and
wherein hydrophilic process, hydrophobic process, or charging process is performed on one region of the substrate or the metal layer, and the molecule recognition functional substances are immobilized at the region not performed with the process.

11. A localized plasmon resonance sensor comprising:
a sensor unit having a metal layer with a plurality of convex parts or concave parts formed by fixing metal particles having a diameter of between 10 and 30 nm at an interval of greater than or equal to two times and less than or equal to four times the diameter in average from each other on a surface of a transparent substrate, and molecule recognition functional substance for attaching a specific analyte immobilized on the substrate or the metal layer;
wherein the surface arranged with the metal layer and the molecule recognition functional substances of the sensor unit is contacted to an analysis sample solution containing analyte modified with a light emitting molecule;
an evanescent light generated at the surface of the substrate by an excitation light irradiated at an incident angle totally reflected at the surface of the substrate onto the other surface of the sensor unit and the metal layer Plasmon resonate to locally intensify an electric field around the metal layer; and presence or concentration of the analyte attached to the molecule recognition functional substance is measured by detecting a luminescent light excited and emitted from the light emitting molecule of the analyte attached to the molecule recognition functional substance among the analytes with the electric field; and wherein the mol concentration of the light emitting molecule is greater than or equal to 100 nM.

12. A localized plasmon resonance sensor comprising:

a sensor unit having a metal layer with a plurality of convex parts or concave parts formed by fixing metal particles having a diameter of between 10 and 30 nm at an interval of greater than or equal to two times and less than or equal to four times the diameter in average from each other on a surface of a transparent substrate, and molecule recognition functional substance for attaching a specific analyte immobilized on the substrate or the metal layer;

wherein the surface arranged with the metal layer and the molecule recognition functional substances of the sensor unit is contacted to an analysis sample solution containing analyte modified with a light emitting molecule;

an evanescent light generated at the surface of the substrate by an excitation light irradiated at an incident angle totally reflected at the surface of the substrate onto the other surface of the sensor unit and the metal layer Plasmon resonate to locally intensify an electric field around the metal layer; and presence or concentration of the analyte attached to the molecule recognition functional substance is measured by detecting a luminescent light excited and emitted from the light emitting molecule of the analyte attached to the molecule recognition functional substance among the analytes with the electric field; and wherein the localized plasmon resonance sensor further comprises a flow path for flowing the analysis sample solution, wherein the molecule recognition functional substances face the inside of the flow path.

13. A localized plasmon resonance sensor comprising:

a sensor unit having a metal layer with a plurality of convex parts or concave parts formed by fixing metal particles having a diameter of between 10 and 30 nm at an interval of greater than or equal to two times and less than or equal to four times the diameter in average from each other on a surface of a transparent substrate, and molecule recognition functional substance for attaching a specific analyte immobilized on the substrate or the metal layer;

wherein the surface arranged with the metal layer and the molecule recognition functional substances of the sensor unit is contacted to an analysis sample solution containing analyte modified with a light emitting molecule;

an evanescent light generated at the surface of the substrate by an excitation light irradiated at an incident angle totally reflected at the surface of the substrate onto the other surface of the sensor unit and the metal layer Plasmon resonate to locally intensify an electric field around the metal layer; and presence or concentration of the analyte attached to the molecule recognition functional substance is measured by detecting a luminescent light excited and emitted from the light emitting molecule of the analyte attached to the molecule recognition functional substance among the analytes with the electric field; and wherein the sensor unit includes a plurality of regions to be introduced with the analysis sample solution, each region being immobilized with the molecule recognition functional substance different from each other.

14. A measurement method using a localized plasmon resonance sensor including a sensor unit having a metal layer with a plurality of convex parts or concave parts formed by fixing metal particles having a diameter of between 10 and 30 nm at an interval of greater than or equal to two times and less than or equal to four times the diameter in average from each other on a surface of a transparent substrate and molecule recognition functional substance for attaching a specific analyte immobilized on the substrate or the metal layer; the method comprising the steps of:

forming an analysis sample solution containing analytes modified by a light emitting molecule by mixing a solution to be measured and a light emitting molecule;

contacting the sample solution to the surface arranged with the metal layer and the molecule recognition functional substances of the sensor unit;

generating an evanescent light at the surface of the substrate by irradiating an excitation light at an incident anile totally reflected at the surface of the substrate to a surface not arranged with the metal layer and the molecule recognition functional substances of the sensor unit;

locally intensifying an electric field around the metal layer by Plasmon resonating the evanescent light and the metal layer; detecting emission intensity of the luminescent light excited and generated from light emitting molecule of the analyte attached to the molecule recognition functional substance among the analytes modified with the light emitting molecules in the sample solution with the electric field; and calculating the presence and the concentration of the analyte from the emission intensity.

15. The measurement method according to claim 14, wherein the solution to be measured is body fluid of human or animal, and the analyte is a biomolecule including at least one of gene, protein, sugar chain or cell.

* * * * *